(12) United States Patent
Michelson

(10) Patent No.: US 7,291,149 B1
(45) Date of Patent: Nov. 6, 2007

(54) METHOD FOR INSERTING INTERBODY SPINAL FUSION IMPLANTS

(75) Inventor: Gary Karlin Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 09/412,082

(22) Filed: Oct. 4, 1999

Related U.S. Application Data

(63) Continuation of application No. 08/480,904, filed on Jun. 7, 1995, now Pat. No. 6,210,412.

(51) Int. Cl.
*A61B 17/56* (2006.01)

(52) U.S. Cl. .......................................... 606/61; 623/17.1

(58) Field of Classification Search ............ 606/60–61; 623/16, 17, 17.1, 17.3
See application file for complete search history.

(56) References Cited

U.S. PATENT DOCUMENTS

| | | |
|---|---|---|
| 350,420 A | 10/1886 | Dillon |
| 1,137,585 A | 4/1915 | Craig |
| 2,065,659 A | 12/1936 | Cullen |
| 2,181,746 A | 11/1939 | Siebrandt |
| 2,243,718 A | 5/1941 | Moreira |
| 2,372,622 A | 3/1945 | Fassio |
| 2,514,665 A | 7/1950 | Myller |
| 2,537,070 A | 1/1951 | Longfellow |
| 2,543,780 A | 3/1951 | Hipps et al. |
| 2,677,369 A | 5/1954 | Knowles |
| 2,774,350 A | 12/1956 | Cleveland |
| 2,789,558 A | 4/1957 | Rush |
| 2,832,343 A | 4/1958 | Mose |
| 2,842,131 A | 7/1958 | Smith |
| 2,878,809 A | 3/1959 | Treace |
| 3,128,768 A | 4/1964 | Geistauts |
| 3,298,372 A | 1/1967 | Feinberg |
| 3,426,364 A | 2/1969 | Lumb |

(Continued)

FOREIGN PATENT DOCUMENTS

CA  1 328 957  5/1994

(Continued)

OTHER PUBLICATIONS

Adams et al.; Outline of Orthopaedics, Eleventh Edition; Trunk and Spine, p. 194.

(Continued)

*Primary Examiner*—Michael A. Brown
(74) *Attorney, Agent, or Firm*—Martin & Ferraro, LLP

(57) ABSTRACT

The present invention is directed to methods of inserting a variety of interbody spinal fusion implants across a disc space between adjacent vertebral bodies. The variety of implants have at least a partially frusto-conical configuration or opposed arcuate portions in an angular relationship to one another along the length of the implant. One of the methods of the present invention contemplates distracting the adjacent vertebral bodies, forming a bore from the anterior or posterior aspect of the spinal column across a distracted disc space between the adjacent vertebral bodies and into the adjacent vertebral bodies, and inserting into the bore the spinal implant having opposed arcuate portions in an angular relationship to one another along the length of the implant and oriented toward the adjacent vertebral bodies.

21 Claims, 16 Drawing Sheets

U.S. PATENT DOCUMENTS

| | | |
|---|---|---|
| 3,486,505 A | 12/1969 | Morrison |
| 3,604,487 A | 9/1971 | Gilbert |
| 3,605,123 A | 9/1971 | Hahn |
| 3,618,611 A | 11/1971 | Urban |
| 3,709,219 A | 1/1973 | Halloran |
| 3,719,186 A | 3/1973 | Merig, Jr. |
| 3,720,959 A | 3/1973 | Hahn |
| 3,750,652 A | 8/1973 | Sherwin |
| 3,848,601 A | 11/1974 | Ma et al. |
| 3,855,638 A | 12/1974 | Pilliar |
| 3,867,728 A | 2/1975 | Stubstad et al. |
| 3,867,950 A | 2/1975 | Fischell |
| 3,875,595 A * | 4/1975 | Froning ............... 623/17 |
| 3,888,260 A | 6/1975 | Fischell |
| 3,892,232 A | 7/1975 | Neufeld |
| 3,905,047 A | 9/1975 | Long |
| 3,906,550 A | 9/1975 | Rostoker et al. |
| 3,915,151 A | 10/1975 | Kraus |
| 3,916,907 A | 11/1975 | Peterson |
| 3,918,440 A | 11/1975 | Kraus |
| 3,942,535 A | 3/1976 | Schulman |
| 3,948,262 A | 4/1976 | Zaffaroni |
| 3,952,334 A | 4/1976 | Bokros et al. |
| 3,987,499 A | 10/1976 | Scharbach et al. |
| 4,016,651 A | 4/1977 | Kawahara et al. |
| 4,027,392 A | 6/1977 | Sawyer et al. |
| D245,259 S | 8/1977 | Shen |
| 4,051,905 A | 10/1977 | Kleine |
| 4,059,115 A | 11/1977 | Jumashev et al. |
| 4,070,514 A | 1/1978 | Entherly et al. |
| 4,082,097 A | 4/1978 | Mann et al. |
| 4,086,701 A | 5/1978 | Kawahara et al. |
| 4,124,026 A | 11/1978 | Berner et al. |
| 4,142,517 A | 3/1979 | Stavropoulos et al. |
| 4,168,326 A | 9/1979 | Broemer et al. |
| 4,175,555 A | 11/1979 | Herbert |
| 4,177,524 A | 12/1979 | Grell et al. |
| 4,181,457 A | 1/1980 | Holmes |
| 4,197,850 A | 4/1980 | Schulman et al. |
| 4,206,516 A | 6/1980 | Pilliar |
| 4,222,128 A | 9/1980 | Tomonaga et al. |
| D257,511 S | 11/1980 | Zahn |
| 4,232,679 A | 11/1980 | Schulman |
| 4,237,948 A | 12/1980 | Jones et al. |
| 4,258,716 A | 3/1981 | Sutherland |
| 4,259,072 A | 3/1981 | Hirabayashi et al. |
| 4,262,369 A | 4/1981 | Roux |
| 4,271,832 A | 6/1981 | Evans et al. |
| D260,525 S | 9/1981 | Lassiter |
| 4,289,123 A | 9/1981 | Dunn |
| 4,293,962 A | 10/1981 | Fuson |
| 4,309,777 A | 1/1982 | Patil |
| 4,328,593 A | 5/1982 | Sutter et al. |
| 4,333,469 A | 6/1982 | Jeffcoat et al. |
| 4,341,206 A | 7/1982 | Perrett et al. |
| 4,349,921 A | 9/1982 | Kuntz |
| 4,356,572 A | 11/1982 | Guillemin et al. |
| 4,401,112 A | 8/1983 | Rezaian |
| 4,405,319 A | 9/1983 | Cosentino |
| 4,414,979 A | 11/1983 | Hirshorn et al. |
| 4,423,721 A | 1/1984 | Otte et al. |
| 4,439,152 A | 3/1984 | Small |
| 4,450,834 A | 5/1984 | Fischer |
| 4,484,570 A | 11/1984 | Sutter et al. |
| 4,492,226 A | 1/1985 | Belykh et al. |
| 4,497,320 A | 2/1985 | Nicholson et al. |
| 4,501,269 A | 2/1985 | Bagby |
| 4,507,115 A | 3/1985 | Kambara et al. |
| RE31,865 E | 4/1985 | Roux |
| 4,530,360 A | 7/1985 | Duarte |
| 4,535,374 A | 8/1985 | Anderson et al. |
| 4,535,485 A | 8/1985 | Ashman et al. |
| 4,542,539 A | 9/1985 | Rowe, Jr. et al. |
| 4,545,374 A | 10/1985 | Jacobson |
| 4,547,390 A | 10/1985 | Ashman et al. |
| 4,549,547 A | 10/1985 | Brighton et al. |
| 4,552,200 A | 11/1985 | Sinha et al. |
| 4,553,273 A | 11/1985 | Wu |
| 4,554,914 A | 11/1985 | Kapp et al. |
| D281,814 S | 12/1985 | Pratt et al. |
| 4,570,623 A | 2/1986 | Ellison et al. |
| 4,570,624 A | 2/1986 | Wu |
| 4,592,346 A | 6/1986 | Jurgutis |
| 4,599,086 A | 7/1986 | Doty |
| 4,600,000 A | 7/1986 | Edwards |
| 4,602,638 A | 7/1986 | Adams |
| 4,604,995 A | 8/1986 | Stephens |
| 4,608,052 A | 8/1986 | Van Kampen et al. |
| 4,611,581 A | 9/1986 | Steffee |
| 4,619,264 A | 10/1986 | Singh |
| 4,628,921 A | 12/1986 | Rousso |
| 4,634,720 A | 1/1987 | Dorman et al. |
| 4,636,217 A | 1/1987 | Ogilvie et al. |
| 4,636,526 A | 1/1987 | Dorman et al. |
| 4,645,503 A | 2/1987 | Lin et al. |
| 4,653,486 A | 3/1987 | Coker |
| 4,655,777 A | 4/1987 | Dunn et al. |
| 4,661,536 A | 4/1987 | Dorman et al. |
| 4,664,567 A | 5/1987 | Edwards |
| 4,665,920 A | 5/1987 | Campbell |
| 4,677,883 A | 7/1987 | Lee |
| 4,677,972 A | 7/1987 | Tornier |
| 4,693,721 A | 9/1987 | Ducheyne |
| 4,696,290 A | 9/1987 | Steffee |
| 4,698,375 A | 10/1987 | Dorman et al. |
| 4,710,075 A | 12/1987 | Davison |
| 4,713,004 A | 12/1987 | Linkow et al. |
| 4,714,469 A | 12/1987 | Kenna |
| 4,721,103 A | 1/1988 | Freedland |
| 4,736,738 A | 4/1988 | Lipovsek et al. |
| 4,743,256 A | 5/1988 | Brantigan |
| 4,743,260 A | 5/1988 | Burton |
| 4,759,766 A | 7/1988 | Buettner-Janz et al. |
| 4,759,769 A | 7/1988 | Hedman et al. |
| 4,769,881 A | 9/1988 | Pedigo et al. |
| 4,781,591 A | 11/1988 | Allen |
| 4,790,303 A | 12/1988 | Steffee |
| 4,805,602 A | 2/1989 | Puno et al. |
| 4,820,305 A | 4/1989 | Harms et al. |
| 4,830,000 A | 5/1989 | Shutt |
| 4,834,757 A | 5/1989 | Brantigan |
| 4,848,327 A | 7/1989 | Perdue |
| 4,851,008 A | 7/1989 | Johnson |
| 4,863,476 A | 9/1989 | Shepperd |
| 4,863,477 A | 9/1989 | Monson |
| 4,865,603 A | 9/1989 | Noiles |
| 4,877,020 A | 10/1989 | Vich |
| 4,878,915 A * | 11/1989 | Brantigan ............... 623/17 |
| 4,903,882 A | 2/1990 | Long |
| 4,904,260 A | 2/1990 | Ray et al. |
| 4,904,261 A | 2/1990 | Dove et al. |
| 4,911,718 A | 3/1990 | Lee et al. |
| 4,913,144 A | 4/1990 | Del Medico |
| 4,936,848 A | 6/1990 | Bagby |
| 4,943,291 A | 7/1990 | Tanguy |
| 4,950,296 A | 8/1990 | McIntyre |
| 4,955,885 A | 9/1990 | Meyers |
| 4,955,908 A | 9/1990 | Frey et al. |
| 4,957,495 A | 9/1990 | Kluger |
| 4,960,420 A | 10/1990 | Goble et al. |
| 4,961,740 A | 10/1990 | Ray et al. |
| 4,968,316 A | 11/1990 | Hergenroeder |
| 4,969,888 A | 11/1990 | Scholten et al. |
| 4,987,904 A | 1/1991 | Wilson |

| | | |
|---|---|---|
| 5,015,247 A | 5/1991 | Michelson |
| 5,015,255 A | 5/1991 | Kuslich |
| 5,026,373 A | 6/1991 | Ray et al. |
| 5,030,236 A | 7/1991 | Dean |
| 5,055,104 A | 10/1991 | Ray |
| 5,059,193 A | 10/1991 | Kuslich |
| 5,062,845 A | 11/1991 | Kuslich et al. |
| 5,071,437 A | 12/1991 | Steffee |
| 5,084,050 A | 1/1992 | Draenert |
| 5,102,414 A | 4/1992 | Kirsch |
| 5,108,422 A | 4/1992 | Green et al. |
| 5,112,336 A | 5/1992 | Krevolin et al. |
| 5,116,304 A | 5/1992 | Cadwell |
| 5,122,130 A | 6/1992 | Keller |
| 5,123,926 A | 6/1992 | Pisharodi |
| 5,171,278 A | 12/1992 | Pisharodi |
| 5,192,327 A | 3/1993 | Brantigan |
| 5,246,458 A | 9/1993 | Graham |
| 5,258,031 A | 11/1993 | Salib et al. |
| 5,263,953 A * | 11/1993 | Bagby ............... 606/612 |
| 5,273,964 A | 12/1993 | Lemons |
| 5,292,252 A | 3/1994 | Nickerson et al. |
| 5,306,309 A | 4/1994 | Wagner et al. |
| 5,314,427 A | 5/1994 | Goble et al. |
| 5,324,295 A | 6/1994 | Shapiro |
| 5,352,229 A | 10/1994 | Goble et al. |
| 5,360,430 A | 11/1994 | Lin |
| 5,364,399 A | 11/1994 | Lowery et al. |
| 5,370,662 A | 12/1994 | Stone et al. |
| 5,370,697 A | 12/1994 | Baumgartner |
| 5,393,036 A | 2/1995 | Sheridan |
| RE34,871 E | 3/1995 | McGuire et al. |
| 5,396,880 A | 3/1995 | Kagan et al. |
| 5,397,359 A | 3/1995 | Mittelmeier et al. |
| 5,397,364 A | 3/1995 | Kozak et al. |
| 5,425,772 A * | 6/1995 | Brantigan ............ 623/17.4 |
| 5,435,723 A | 7/1995 | O'Brien |
| 5,443,514 A | 8/1995 | Steffee |
| 5,458,638 A | 10/1995 | Kuslich et al. |
| 5,489,307 A | 2/1996 | Kuslich et al. |
| 5,489,308 A | 2/1996 | Kuslich et al. |
| 5,571,109 A | 11/1996 | Bertagnoli |
| 5,571,190 A | 11/1996 | Ulrich et al. |
| 5,609,635 A | 3/1997 | Michelson |
| 5,669,909 A * | 9/1997 | Zdeblick ............... 606/72 |
| 5,683,463 A | 11/1997 | Godefroy et al. |
| 5,766,252 A | 6/1998 | Henry et al. |
| 5,782,919 A | 7/1998 | Zdeblick et al. |
| D397,439 S | 8/1998 | Koros et al. |
| 5,800,547 A | 9/1998 | Schafer et al. |
| 5,906,616 A | 5/1999 | Pavlov et al. |
| 6,210,412 B1 * | 4/2001 | Michelson ............ 606/61 |

FOREIGN PATENT DOCUMENTS

| | | | |
|---|---|---|---|
| CA | 2 151 481 | 3/1995 | |
| DE | 1 961 531 | 7/1970 | |
| DE | 24 46 039 | 4/1975 | |
| DE | 2 910 627 | 9/1980 | |
| DE | 31 01 333 A1 | 12/1981 | |
| DE | 31 32 520 A1 | 6/1982 | |
| DE | 35 05 567 A1 | 6/1986 | |
| DE | 36 08 163 A1 | 9/1987 | |
| DE | 3 620 549 | 12/1987 | |
| DE | 41 04 359 A1 | 8/1992 | |
| DE | 43 02 397 A1 | 7/1993 | |
| EP | 0 077 159 | 4/1983 | |
| EP | 0 179 695 | 9/1985 | |
| EP | 0 162 005 | 11/1985 | |
| EP | 0 260 044 | 8/1988 | |
| EP | 0 303 241 A2 | 2/1989 | |
| EP | 0 307 241 | 3/1989 | |
| EP | 0 493 698 A1 | 7/1992 | |
| EP | 0 499 465 A1 | 8/1992 | |
| EP | 0 526 682 | 2/1993 | |
| EP | 0 551 187 A1 | 7/1993 | |
| EP | 0 577 179 A1 | 1/1994 | |
| EP | 0 599 419 A2 | 6/1994 | |
| EP | 0 627 204 A2 | 12/1994 | |
| EP | 0 637 439 | 2/1995 | |
| EP | 0 637 440 | 2/1995 | |
| EP | 0 646 366 | 4/1995 | |
| EP | 0 732 093 A2 | 9/1996 | |
| ES | 283078 | 5/1985 | |
| FR | 2 295 729 | 7/1976 | |
| FR | 0 179 695 | 4/1986 | |
| FR | 2 581 336 | 11/1986 | |
| FR | 2 703 580 | 10/1994 | |
| GB | 2076657 A | 12/1981 | |
| GB | 2082754 A | 3/1982 | |
| GB | 2126094 A | 3/1984 | |
| GB | 2164277 A | 3/1986 | |
| JP | 57-29348 | 2/1982 | |
| JP | 60-31706 | 2/1985 | |
| JP | 60-43984 | 3/1985 | |
| JP | 61-122859 | 6/1986 | |
| JP | 62-155846 | 7/1987 | |
| SE | 106 101 | 7/1939 | |
| SU | 1107854 | 8/1984 | ............... 623/17 |
| SU | 1124960 | 11/1984 | |
| SU | 1217374 | 3/1986 | |
| SU | 1222254 | 4/1986 | |
| WO | 84/01298 | 4/1984 | |
| WO | 91/06266 | 5/1991 | |
| WO | 92/14423 | 9/1992 | |
| WO | 93/01771 | 2/1993 | |
| WO | 96/22747 | 8/1996 | |

OTHER PUBLICATIONS

Albrektsson, T., et al.; Osseointegrated Titanium Implants; Acta. Orthop. Scand.; vol. 52:155-170 (1981).

Bagby, George W.; Wobbler Syndrome in Horses (the Ataxic Horse); Spokane County Medical Society Bulletin; Spring 1979.

Bagby, Goerge W.; Basket Implant Facilitates Spinal Fusion; Orthopedics Today, vol. 7, No. 10 (Oct. 1987).

Bagby, George W.; Arthrodesis by the Distraction-Compressiion Method Using a Stainless Steel Implant; Orthopedics, vol. II, No. 6, pp. 931-934 (Jun. 1987).

Brandt, L., et al.; A Dowell Inserter for Anterior Cervical Interbody Fusion; J. Neurosurg. 61:793-794 (Oct. 1984).

Butts, M.K., et al.; Biomechanical Analysis of a New Method for Spinal Interbody Fixation; 1987 Symposium, American Society of Mechanical Engineers, "Advances in Bioengineering", Boston, MA (Dec. 13-18, 1987).

Crawley et al.; A Modified Cloward's Technique for Arthrodesis of the Normal Metacarpophalangeal Joint in the Horse; Veterinary Surgery, vol. 17, No. 3, pp. 117-127 (1988).

Crock, Henry V.; Practice of Spinal Surgery; Springer-Verlag/Wien, New York (1983).

Danek Group, Inc.; Spine Basics, Glossary (1993).

DeBowes, R.M., et al.; Study of Bovine . . . Steel Baskets; Transactions of the 29th Annual Meeting; Orthopaedic Research Society, vol. 8, p. 407, Mar. 8-10, (1983).

EBI Medical Systems; The SpF-T Spinal Fusion Stimulator: An Efficacious Adjunct that Meets the Diverse Needs of Spine Patients; (Aug. 1991).

EBI Medical Systems; The Use of Direct Current for Electrically Induced Osteogenesis: The Positive Effect of an Electronegative Charge on Bone Growth; (Feb. 1993).

European Search Report dated Aug. 4, 1999 for European Patent Application No. 96917084 in the name of Gary Karlin Michelson.

European Search Report dated Jan. 12, 2000 for European Patent Application No. 96918001 in the name of Gary Karlin Michelson.

Gillingham, F.J., et al.; Automatic Patient Monitoring in the Ward; Brit. J. Surg., vol. 53, No. 10, pp. 864-866 (Oct. 1966).

Gillingham, F.J., et al.; Head Injuries: Proceedings of the 18th World Congress of the International College of Surgeons, Rome, pp. 68-71 (May 28-31, 1972).

Goldthwaite, N., et al.; Toward Percutaneous Spine Fusion; Ch. 45; Lumbar Spine Surgery; C.V. Mosby Company, pp. 512-522 (1987).

Harris, P., et al.; Spinal Deformity After Spinal Cord Injury; Paraplegia, vol. 6, No. 4, pp. 232-238 (Feb. 1969).

Herkowitz et al.; Principles of Bone Fusion; The Spine, Third Edition; Chapter 44, p. 1739.

Itoman, M., et al.; Banked Bone Grafting for Bone Defect Repair—Clinical Evaluation of Bone Union and Graft Incorporation; J. Jpn. Orthop. Assoc. 62:461-469 (1988).

Kane, W.J.; Direct Current Electrical Bone Growth Stimulation for Spinal Fusion; Spine; vol. 13, No. 3, pp. 363-365 (Mar. 1988).

Lumbar Spine Surgery, Techniques & Complications; History of Lumbar Spine Surgery (1994) pp. 11-15; 27; 30; 35-45; 265-268.

Maloney, A.F.J., et al.; Clinical and Pathological Observations in Fatal Head Injuries; Brit. J. Surg., vol. 56, No. 1, pp. 23-31 (Jan. 1969).

Morscher, E., et al.; Die vordere Verplattung der Halswirbelsaule mit dem Hohlschrauben-Plattensystem aus Titanium; Der Chirurg. vol. 57, pp. 702-707 (1986) with English Translation.

Muschler et al.; The Biology of Spinal Fusion; Spinal Fusion Science and Technique. Cotler and Cotler, pp. 9-13.

Mylonas, C., et al.; Anterior Cervical Decompression and Fusion Using the Coventry Cervical Spreader and Dowel Inserter; British Journal of Neurosurgery; 7:545-549 (1993).

O'Neill, P., et al.; Spinal Meningoceles in Association with Neurofibromatosis; Neurosurgery, vol. 13, No. 1, pp. 82-84 (Jul. 1983).

Otero-Vich, Jose M.; Anterior Cervical Interbody Fusion with Threaded Cylindrical Bone; J. Neurosurg 63:750-753 (Nov. 1985).

Rathke, F.W., et al.; Surgery of the Spine; Atlas of Orthopaedic Operations, vol. 1, p. 137, W.B. Saunders Co., Philadelphia (1979).

Raveh, J., et al., Neue Rekonstruktionsmaglichkeiten des Unterkiefers bei knochernen Defekten nach Tumorresektionen; Der Chirurg vol. 53:459-467 (1982).

Raveh, J., et al.; Use of the Titanium-coated Hollow Screw and Reconstruction Plate System in Bridging of Lower Jaw Defects; J. Oral Maxillofac Surg. 42:281-294 (1984).

Raveh, J., et al.; Surgical Procedures for Reconstruction of the Lower Jaw Using the Titanium-Coated Hollow-Screw Reconstruction Plate System: Bridging of Defects; Otolaryngologic Clinics of North America; vol. 20, No. 3 (Aug. 1987).

Schmitz et al.; Performance of Alloplastic Materials and Design of an Artificial Disc; The Artificial Disc; Brock, Mayer, Weigel; pp. 23-34 (1991).

Thieme; Fusion of the Lumbar Spine; Anterior Monosegmental Fusion L5-S1; Atlas of Spinal Operations, pp. 270-274 (1993).

Whatmore, W.J.; Sincipital Encephalomeningoceles; Brit. J. Surg., vol. 60, No. 4, pp. 261-270 (Apr. 1973).

Whatmore, W.J.; Meningioma Following Trauma; Brit. J. Surg., vol. 60, No. 6, pp. 496-498 (Jun. 1973).

Whatmore, W.J.; The Coventry Cervical Spreader and Dowell Inserter; ACTA Neurochirurgica, vol. 70, FASC. 1-2 (1984).

Whatmore, W.J.; Proceedings of the Society of British Neurological Surgeons; Journal of Neurology, Neurosurgery, and Phychiatry, 50:1093-1100 (1987).

Zindrick et al.; Lumbar Spine Fusion: Different Types and Indications; The Lumbar Spine, vol. 1, Second Edition, pp. 588-593 (1996).

Cloward, Ralph B.; Surgical Techniques for Lumbar Disc Lesions; Codman; Signature Serial 3.

Cloward, Ralph B.; Ruptured Cervical Intervertebral Discs: Removal of Disc & Osteophytes & Anterior Cervical Interbody Fusion (A.C.I.F.); Codman; Signature Series 4.

Cloward, Ralph B.; Recent Advances in Surgery of the Cervical Spine; pp. 285-293; German Society For Neurosurgery: vol. 2 Cervical Spine Operations; Excerpta Medica.

Hutter, Charles George; Spinal Stenosis and Posterior Lumbar Interbody Fusion; pp. 103-114; Clinical Orthopaedics and Related Research; No. 193; The Association of Bone and Joint Surgeons.

Lin, Paul M.; Posterior Lumbar Interbody Fusion; pp. 114-122; Charles C. Thomas; Springfield, Illinois.

Lin, Paul M.; Lumbar Interbody Fusion: Principles and Techniques in Spine Surgery; Techniques and Complications; pp. 81, 98, 120, 146, 173, 180-184, 204, 224, 225, 231; Aspen Publishers, Inc.; 1989.

Tan, S.B.; A Modified Technique of Anterior Lumbar Fusion with Femoral Cortical Allograft; pp. 83-93; The Journal of Orthopaedic Surgical Techniques, vol. 5, No. 3, 1990.

Muller, M.E.; Manual of Internal Fixation: Techniques Recommended by the AO Group; Second Edition, Expanded and Revised; pp. 3-20, 27-41, 53-58, 71-78, 94, 311, 320; Springer-Verlag; 1979.

Hierholzer, G.; Manual on the AO/ASIF Tubular External Fixator; pp. 85-91, Springer-Verlag; 1985.

Heim, Urs; Small Fragment Set Manual: Technique Recommended by the ASIF-Group; pp. 5-7, 10, 20, 21, 30; Springer-Verlag; 1974.

Harmon, Paul H.; Anterior Excision and Vertebral Body Fusion Operation for Intervertebral Disk Syndromes of the Lower Lumbar Spine: Three- to Five-Year Results in 244 Cases; pp. 107-127; Clinical Orthopaedics and Related Research, No. 26, J.B. Lippincott Company, 1963.

Harmon, Paul H.; A Simplified Surgical Technic for Anterior Lumbar Diskectomy and Fusion; Aviodance of Complications; Anatomy of the Retroperitoneal Veins; pp. 130-143; Clinical Orthopaedics and Related Research, No. 37, J.B. Lippincott Company, 1964.

Bullough, Peter G.; Atlas of Spinal Diseases; Figure 5.7; J.B. Lippencott Company; 1988.

Canale, S. Terry; Campbell's Operative Orthopaedics; vol. 3, 9th Edition; pp. 2191, 2216, 2459; Mosby, 1998.

Tech. Mitt. Krupp, "Nickel-Titanium Spacers For Partial Stiffening Of The Spinal Column—Problems Involved, Manufacture, Pretesting, And Clinical Use"; vol. 42 (1984), No. 1, pp. 24-38; including translation pp. 5-27.

* cited by examiner

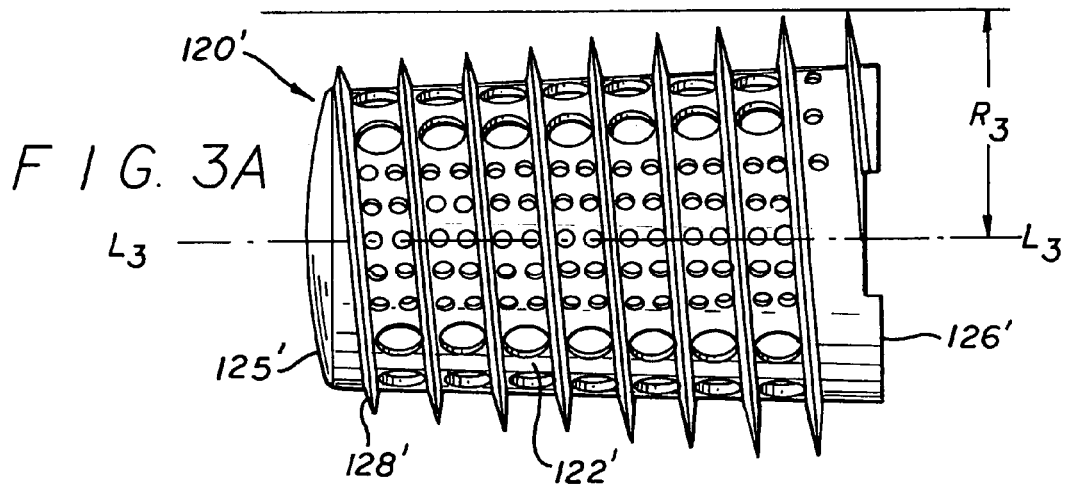
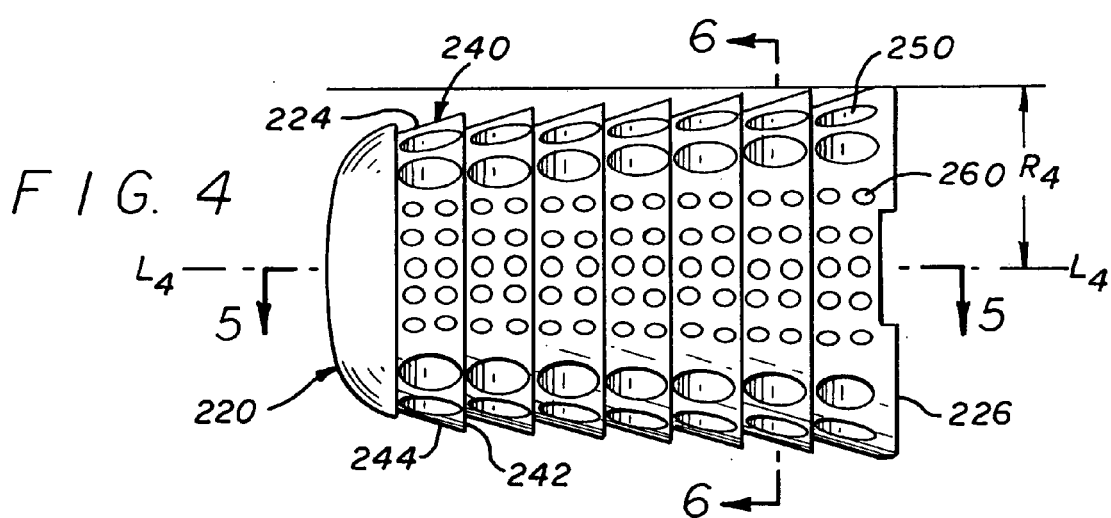
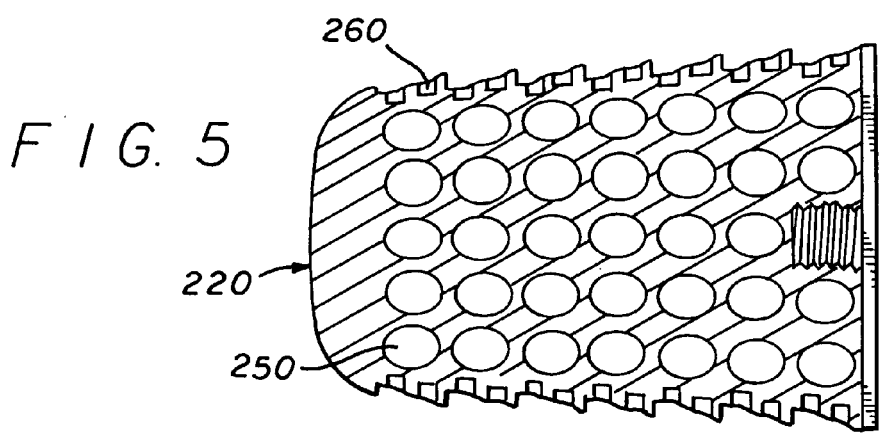

METHOD FOR INSERTING INTERBODY SPINAL FUSION IMPLANTS

RELATED APPLICATIONS

This application is a continuation of application Ser. No. 08/480,904, filed Jun. 7, 1995, now U.S. Pat. No. 6,210,412.

BACKGROUND OF THE INVENTION

1. Field of the Invention

The present invention relates generally to a method for inserting interbody spinal fusion implants, and in particular to a method for inserting spinal fusion implants configured to restore and maintain two adjacent vertebrae of the spine in anatomical lordosis.

2. Description of the Related Art

Interbody spinal fusion refers to the method of achieving bony bridging between adjacent vertebrae through the disc space, the space between adjacent vertebrae normally occupied by a spinal disc. Numerous implants to facilitate such a fusion have been described by Cloward, Brantigan, and others, and are known to those skilled in the art. Generally, cylindrical implants offer the advantage of conforming to an easily prepared recipient bore spanning the disc space and penetrating into each of the adjacent vertebrae. Such a bore may be created by use of a drill. It is an anatomical fact that both the cervical spine and the lumbar spine are normally lordotic, that is convex forward. Such alignment is important to the proper functioning of the spine. Commonly, those conditions which require treatment by spinal fusion are associated with a loss of lordosis.

Michelson, in U.S. patent application Ser. No. 08/396,414, now U.S. Pat. No. 6,080,155, entitled METHOD OF INSERTING AND PRELOADING SPINAL IMPLANTS, teaches a method for restoring the anatomical lordosis of the spine while performing the interbody fusion procedure. While this has been a significant advance over prior methods, it has nevertheless been associated with a sometimes less than desirable consequence, that being the uneven removal of bone from each of the adjacent vertebrae relative to the vertebral endplates adjacent the disc space.

Therefore, there exists a need for spinal fusion implants and instrumentation that permits for the uniform depth of bone removal from each of the adjacent vertebrae while restoring anatomical lordosis.

SUMMARY OF THE INVENTION

The present invention is directed to a method for inserting a variety of interbody spinal fusion implants having at least a partially frusto-conical configuration to achieve a desired anatomical lordosis of the spine. In the preferred embodiment of the method of the present invention, the spinal fusion implants being inserted have an outer locus in which at least some of the points of the implant comprise a partially or fully frusto-conical shape substantially along the portion of the implant in contact with the adjacent vertebrae of the spine and have an insertion end and a trailing end. The spinal fusion implants may be further modified so that while the upper and lower surfaces are portions of a frusto-cone, or a cylinder at least one side portion may be truncated to form a planar surface that is parallel to the central longitudinal axis of the implant to form straight walls. These implants may have a more tapered aspect at the insertion end of the implant to facilitate insertion. The spinal fusion implants of the present invention may be relatively solid and/or porous and/or hollow, and may have surface roughenings to promote bone ingrowth and stability.

In the preferred method of the present invention, the diseased disc between two vertebrae is at least partially removed. The two vertebrae adjacent the diseased disc are then optimally distracted and placed in the desired amount of lordosis by any of a number of well known means including, but not limited to, those means that distract the vertebral bodies by engaging screws placed into the anterior aspect of the vertebral bodies, and disc space distractors that are placed from the anterior aspect of the spine into the disc space and are then used to urge the vertebral endplates away from each other and into lordosis. When the correct amount of distraction and lordosis have been achieved at the affected disc level, then a frusto-conical space is created from anterior to posterior between the adjacent vertebrae. The frusto-conical space that is created is greater in diameter than the disc space height, such that some bone is removed from each of the adjacent vertebrae. The created space is generally frusto-conical in shape, being greatest in diameter anteriorly and tapering to a lesser diameter posteriorly.

In an alternative method of implant insertion, the use of at least partially frusto-conical interbody spinal fusion implants allows for the creation of lordosis by the implant itself where none is present to begin with. The disc space which in the preferred circumstance would be fully distracted but need not be, but lacking lordosis, could have a bore drilled across that space such that equal arcs of bone are removed from each of the adjacent vertebrae using a drill or bone milling device capable of producing a cylindrical bore. The vertebrae, whether distracted from each other or not, are essentially lacking the full restoration of lordosis. The use of the substantially cylindrical bone drill provides for the removal of a generally uniform thickness of bone from each of the adjacent vertebrae from anterior to posterior. The insertion of a frusto-conical implant, having a larger diameter at its trailing edge than at its leading edge, then forces the anterior aspects of the adjacent vertebrae apart more so than the posterior aspects where the diameter is lesser. This utilizes the implant to produce the desired lordosis.

To further assist incorporation into the spinal fusion bone mass, the spinal fusion implants of the present invention may have wells extending into the material of the implant from the surface for the purpose of holding fusion promoting materials and to provide for areas of bone ingrowth fixation. These wells, or holes, may pass either into or through the implant and may or may not intersect. The spinal fusion implants of the present invention may have at least one chamber which may be in communication through at least one opening to the surface of the implant. Said chamber may have at least one access opening for loading the chamber with fusion promoting substances. The access opening may be capable of being closed with a cap or similar means. Still further, a variety of surface irregularities may be employed to increase implant stability and implant surface area, and/or for the purpose of advancing the spinal fusion implant into the fusion site such as a thread. The exterior of the spinal fusion implant of the present invention may have wholly or in part, a rough finish, knurling, forward facing ratchetings, threads or other surface irregularities sufficient to achieve the purpose described.

The spinal fusion implants of the present invention offer significant advantages over the prior art implants:

1. Because the spinal fusion implants of the present invention are at least partially frusto-conical in shape, those that taper from the leading edge to the trailing edge they are easy to introduce and easy to fully insert into the spinal segment to be fused. In the preferred embodiment, where the leading edge of the implant is larger than the trailing edge, the implant utilizes a tapered forward portion and an increasing thread height relative to the body from the leading edge to the trailing edge to facilitate insertion.

2. The shape of the implants of the present invention is consistent with the shape of the disc, which the implants at least in part replace, wherein the front of the disc is normally taller than the back of the disc, which allows for normal lordosis. The implants of the present invention are similarly taller anteriorly than they are posteriorly.

3. The spinal fusion implants of the present invention allow for a minimal and uniform removal of bone from the vertebrae adjacent the disc space while still providing for an interbody fusion in lordosis when properly inserted.

4. The spinal fusion implants of the present invention conform to a geometric shape, which shape is readily producible at the site of fusion, to receive said spinal fusion implants.

The spinal fusion implants of the present invention can be made of any material appropriate for human implantation and having the mechanical properties sufficient to be utilized for the intended purpose of spinal fusion, including various metals such as cobalt chrome, stainless steel or titanium including its alloys, various plastics including those which are bio-absorbable, and various ceramics or combination sufficient for the intended purpose. Further, the spinal fusion implants of the present invention may be made of a solid material, a mesh-like material, a porous material and may comprise, wholly or in part, materials capable of directly participating in the spinal fusion process, or be loaded with, composed of, treated or coated with chemical substances such as bone, morphogenic proteins, hydroxyapatite in any of its forms, and osteogenic proteins, to make them bioactive for the purpose of stimulating spinal fusion. The implants of the present invention may be wholly or in part bioabsorbable.

OBJECTS OF THE PRESENT INVENTION

It is an object of the present invention to provide a method for inserting frusto-conical spinal fusion implants into the spine;

It is yet another object of the present invention to provide a method for inserting frusto-conical spinal fusion implants that are capable of maintaining anatomic alignment and lordosis of two adjacent vertebrae during the spinal fusion process;

It is yet another object of the present invention to provide a method for inserting frusto-conical spinal fusion implants that is capable of providing stability between adjacent vertebrae when inserted;

It is further another object of the present invention to provide a method of inserting frusto-conical spinal fusion implants that includes spacing apart and supporting adjacent vertebrae;

It is still further another object of the present invention to provide a method for inserting frusto-conical spinal fusion implants that is consistent in use with the preservation of a uniform thickness of the subchondral vertebral bone;

It is another object of the present invention to provide a method for inserting frusto-conical spinal fusion implants having a shape which conforms to an easily produced complementary bore at the fusion site; and It is a further object of the present invention to provide a method for inserting a frusto-conical spinal fusion implant which may be placed side by side adjacent to a second identical implant across the same disc space, such that the combined width of the two implants is less than sum of the individual heights of each implant.

These and other objects of the present invention will become apparent from a review of the accompanying drawings and the detailed description of the drawings.

BRIEF DESCRIPTION OF THE DRAWINGS

FIG. 3A is an alternative embodiment of the spinal fusion implant having a frusto-conical body with an external thread radius and thread height that are not constant.

FIG. 4 is a side elevational view of an alternative embodiment of the spinal fusion implant having a frusto-conical body and a surface configuration comprising ratchetings for engaging bone, with wells and channels for bone ingrowth.

FIG. 5 is a cross sectional view along line 5—5 of the implant of FIG. 4 illustrating the channels and wells of the implant.

DETAILED DESCRIPTION OF THE DRAWINGS

The first part of the Detailed Description Of The Drawings is directed to the description of the structure of the frusto-conical implants inserted by the method of the present invention. The second part of the description of the drawings is directed to the method of the present invention.

Frusto-Conical Implants

Figure 1:
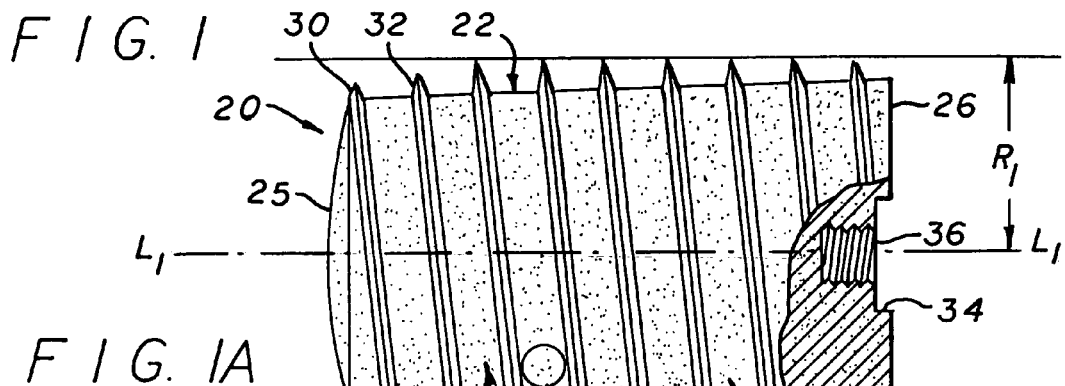
FIG. 1 is a side elevational view of a frusto-conical spinal fusion implant having a body that is frusto-conical with an external thread having a substantially uniform radius.

Referring to FIG. 1, a side elevational view of the spinal fusion implant for insertion with the method of the present invention generally referred to by numeral 20 is shown. The implant 20 has a body 22 that is frusto-conical in shape such that the body 22 has a diameter (root diameter) that is generally frusto-conical. The body 22 has an insertion end 24 and a trailing end 26. The insertion end 24 may include a tapered portion 25 to facilitate insertion of the spinal implant 20. In the preferred embodiment, when the implant 20 is inserted from the anterior aspect of the spine, the body 22 of the implant 20 has a maximum diameter at a point nearest to the trailing end 26 and a minimum diameter at a point nearest to the insertion end 24.

The implant 20 has an external thread 28 having a substantially uniform radius $R_1$ measured from the central longitudinal axis $L_1$ of the implant 20. The outer locus of the external thread 28 (major diameter) has an overall configuration that is substantially parallel to the longitudinal axis $L_1$. While the major diameter of the implant 20 is substantially uniform, the external thread 28 may be modified at the leading edge by having initially a reduced thread radius to facilitate insertion of the implant 20 and may also be modified to make the external thread 28 self-tapping. In the preferred embodiment, the external thread 28 has a first thread 30 of a lesser radius than the radius $R_1$ of the remainder of the external thread 28 to facilitate insertion of the implant 20. The second thread 32 has a greater radius than the first thread 30, but is still shorter than the radius $R_1$ of the remainder of the external thread 28 which is thereafter of constant radius.

The body 22 is frusto-conical substantially along the portion of the body 22 in contact with the adjacent vertebrae of the spine which allows for the creating and maintaining of the adjacent vertebrae of the spine in the appropriate angular relationship to each other in order to preserve and/or restore the normal anatomic lordosis of the spine. The substantially uniform radius $R_1$ of the external thread 28 of the implant 20 allows for the engaging of the bone of the adjacent vertebrae in a position that counters the forces which tend to urge the implant 20 from between the adjacent vertebrae in the direction opposite to which the implant 20 was implanted. The greater thread height measured from the body 22 near the leading end 24 of the implant 20 provides greater purchase into the vertebral bone and again enhances the stability of the implant 20. Further, the configuration of the external thread 28 increases the surface area of the implant 20 in contact with the vertebrae to promote bone ingrowth.

The implant 20 has a recessed slot 34 at its trailing end 26 for receiving and engaging insertion instrumentation for inserting the implant 20. The recessed slot 34 has a threaded opening 36 for threadably attaching the implant 20 to instrumentation used for inserting the implant 20.

Figure 1A:
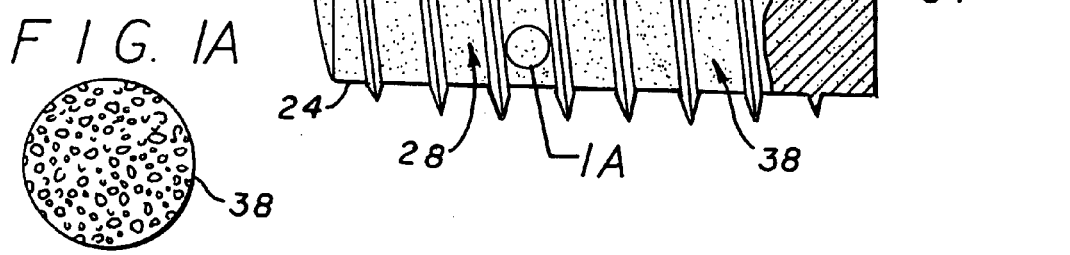
FIG. 1A is an enlarged fragmentary view along line 1A of FIG. 1 illustrating the surface configuration of the implant of FIG. 1.
Figure 2:
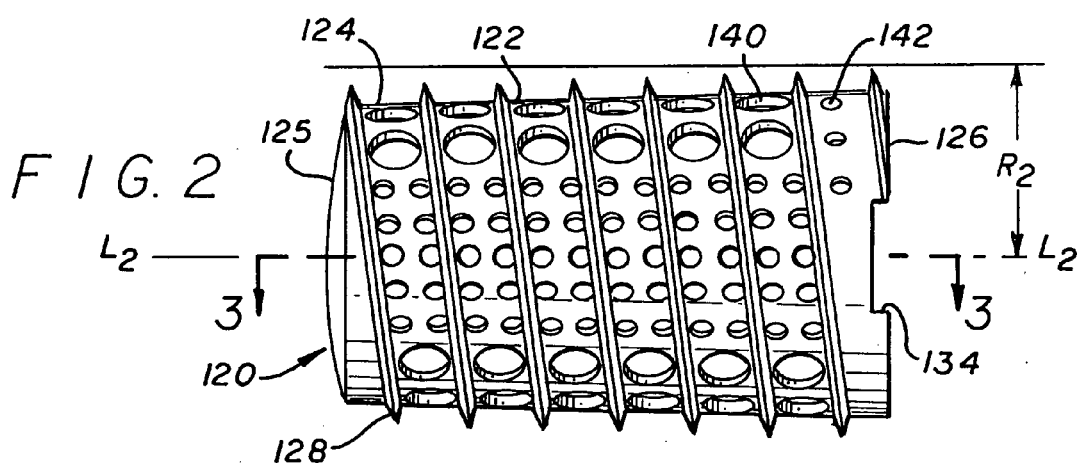

Referring to FIG. 1A, the implant 20 has an outer surface 38 that is porous to present an irregular surface to the bone to promote bone ingrowth. The outer surface 38 is also able to hold fusion promoting materials and provides for an increased surface area to engage the bone in the fusion process and to provide further stability. It is appreciated that the outer surface 38, and/or the entire implant 20, may comprise any other porous material or roughened surface sufficient to hold fusion promoting substances and/or allow for bone ingrowth and/or engage the bone during the fusion process. The implant 20 may be further coated with bioactive fusion promoting substances including, but not limited to, hydroxyapatite compounds, osteogenic proteins and bone morphogenic proteins. The implant 20 is shown as being solid, however it is appreciated that it can be made to be substantially hollow or hollow in part.

In the preferred embodiment, for use in the lumbar spine, the implant 20 has an overall length in the range of approximately 24 mm to 32 mm with 26 mm being the preferred length. The body 22 of the implant 20 has a root diameter at the insertion end 24 in the range of 8–20 mm, with 14–16 mm being the preferred root diameter at the insertion end, and a root diameter at the trailing end 26 in the range of 10–24 mm, with 16–18 mm being the preferred diameter at the trailing end 26, when said implants are used in pairs. When used singly in the lumbar spine, the preferred diameters would be larger.

In the preferred embodiment, the implant 20 has a thread radius $R_1$ in the range of 6 mm to 12 mm, with 9–10 mm being the preferred radius $R_1$. For use in the cervical spine, the implant 20 has an overall length in the range of approximately 10–22 mm, with 12–14 mm being the preferred length. The body 22 of the implant 20 has a root diameter at the insertion end 24 in the range of 8–22 mm, with 16–18 mm being the preferred root diameter at the insertion end when used singly, and 8–10 mm when used in pairs. The body 22 of the implant 20 has a root diameter at the trailing end 26 in the range of 10–24 mm, with 18–20 mm being the preferred root diameter at the trailing end 26 when used singly, and 10–12 mm when used in pairs; a thread radius $R_1$ in the range of approximately 4–12 mm, with 9–10 mm being the preferred radius $R_1$ when inserted singularly and 5–7 mm when inserted side by side in pairs.

Figure 3:
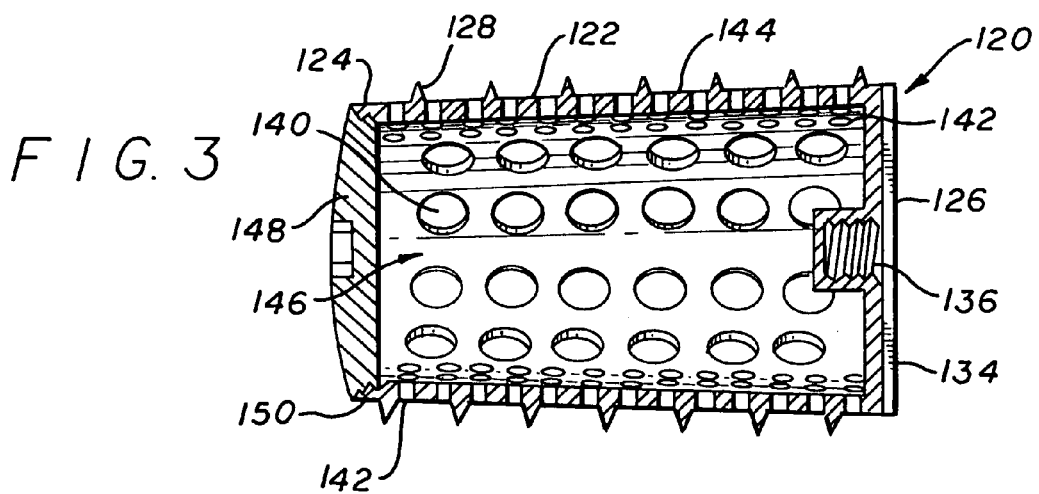
FIG. 3 is as cross sectional view along line 3—3 of the implant of FIG. 3A.

Referring to FIG. 3, a cross sectional view along line 3—3 of the implant 120 is shown. The implant 120 has an outer wall 144 surrounding an internal chamber 146. The large and small openings 140 and 142 may pass through the outer wall 144 to communicate with the internal chamber 146. The internal chamber 146 may be filled with bone material or any natural or artificial bone growth material or fusion promoting material such that bone growth occurs from the vertebrae through the openings 140 and 142 to the material within internal chamber 146. While the openings 140 and 142 have been shown in the drawings as being circular, it is appreciated that the openings 140 and 142 may have any shape, size configuration or distribution, suitable for use in a spinal fusion implant without departing from the scope of the present invention.

The implant 120 has a cap 148 with a thread 150 that threadably attaches to the insertion end 124 of the spinal fusion implant 120. The cap 148 is removable to provide access to the internal chamber 146, such that the internal chamber 146 can be filled and hold any natural or artificial osteoconductive, osteoinductive, osteogenic, or other fusion enhancing material. Some examples of such materials are bone harvested from the patient, or bone growth inducing material such as, but not limited to, hydroxyapatite, hydroxyapatite tricalcium phosphate; or bone morphogenic protein. The cap 148 and/or the spinal fusion implant 120 may be made of any material appropriate for human implantation including metals such as cobalt chrome, stainless steel, titanium, plastics, ceramics, composites and/or may be made of, and/or filled, and/or coated with a bone ingrowth inducing material such as, but not limited to, hydroxyapatite or hydroxyapatite tricalcium phosphate or any other osteoconductive, osteoinductive, osteogenic, or other fusion enhancing material. The cap 148 and the implant 120 may be partially or wholly bioabsorbable.

Referring to FIG. 3A, an alternative embodiment of implant 120 is shown and generally referred to by the numeral 120'. The implant 120' has a body 122' similar to body 122 of implant 120 and has an external thread 128' having a radius $R_3$ measured from the central longitudinal axis $L_3$ of the implant 120'. The thread radius $R_3$ is not constant throughout the length of the implant 120' and the external thread 128' has a thread height that is also not constant with respect to the body 122' of the implant 120'. In the preferred embodiment, the implant 120' has an external thread 128' with a radius $R_3$ that increases in size from the insertion end 124' to the trailing end 126' of the implant 120'.

Referring to FIG. 4, an alternative embodiment of the spinal fusion implant of the present invention is shown and generally referred to by the numeral 220. The implant 220 has a frusto-conical body 222 and an outer locus that is generally frusto-conical substantially along the portion of the implant 220 that is in contact with the adjacent vertebrae of the spine. The implant 220 has a surface configuration of forward facing ratchetings 240 suitable for engaging the bone of the adjacent vertebrae. Each of the plurality of ratchetings 240 has a bone engaging edge 242 and ramped portion 244. The ratchetings 240 have a radius $R_4$ measured from the central longitudinal axis $L_4$ of the implant 220 that increases from the insertion end 224 to the trailing end 226. The height of the ratchetings 240 measured from the body 222 is constant throughout the length of implant 220.

The orientation of the ratchetings 240 makes the insertion of the implant 220 easier than its removal, as the ramped portions 244 act as an inclined plane on the way in, while the bone engaging edges 242 resist motion in the opposite directions. These forward facing ratchetings 240 tend to urge the implant 220 forward until the unremoved bone of the vertebrae blocks further motion resulting in a very stable spine and implant construct.

In the preferred embodiment, the bone engaging edges 242 of the ratchetings 240 have a height at a highest point measured from the body 222 (root diameter) of the implant 220 in the range of 0.25–2.0 mm, with the preferred height being 0.4 mm for use in the cervical spine and 1.25 mm for use in the lumbar spine.

Figure 6:
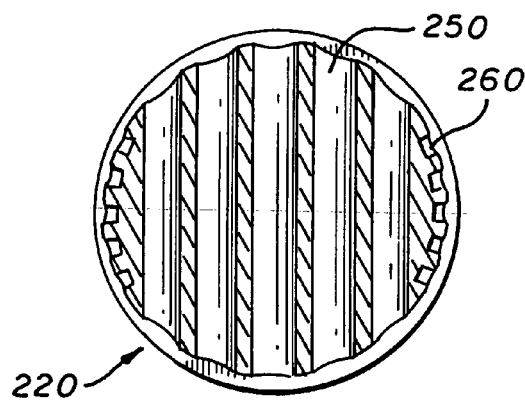
FIG. 6 is a cross sectional view along line 6—6 of the implant of FIG. 4 illustrating the channels and wells of the implant.

Referring to FIGS. 5 and 6, cross sectional views of implant 220 are shown. The implant 220 has channels 250 passing through the implant 220 and wells 260 formed in the surface of the implant 220. The wells 260 may or may not communicate with the channels 250. In the preferred embodiment of implant 220, the channels 250 have a diameter in the range of 0.1 mm to 6 mm, with 2–3 mm being the preferred diameter. The wells 260 have a diameter in the range of 0.1 mm to 6 mm, with 1–3 mm being the preferred diameter range. It is appreciated that although the channels 250 and wells 260 are shown having a generally rounded configuration, it is within the scope of the present invention that the channels 250 and wells 260 may have any size, shape, configuration, and distribution suitable for the intended purpose.

Figure 6A:
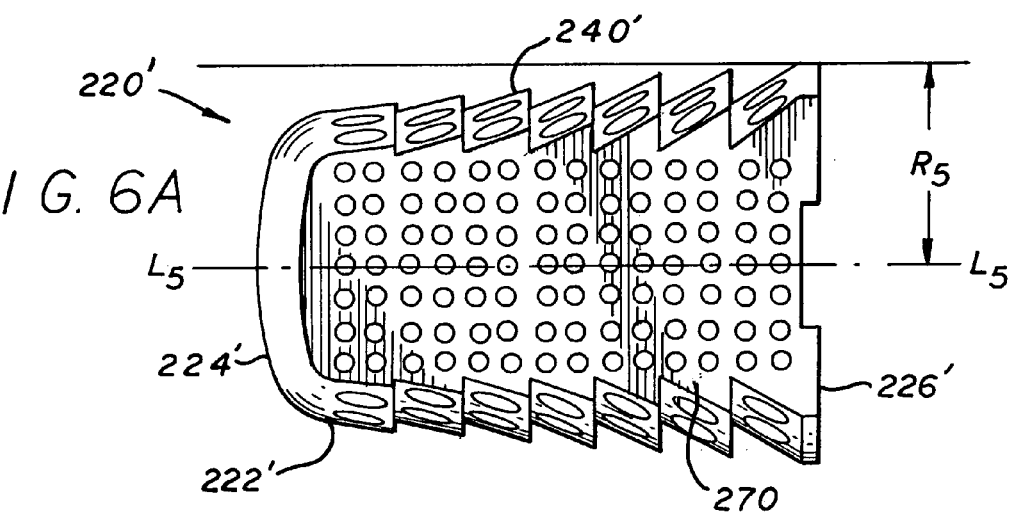
FIG. 6A is a side elevational view of an alternative embodiment of the spinal fusion implant having truncated sides forming a planar surface parallel to the longitudinal axis of the implant and ratchetings having a radius and height that are not constant.
Figure 6B:
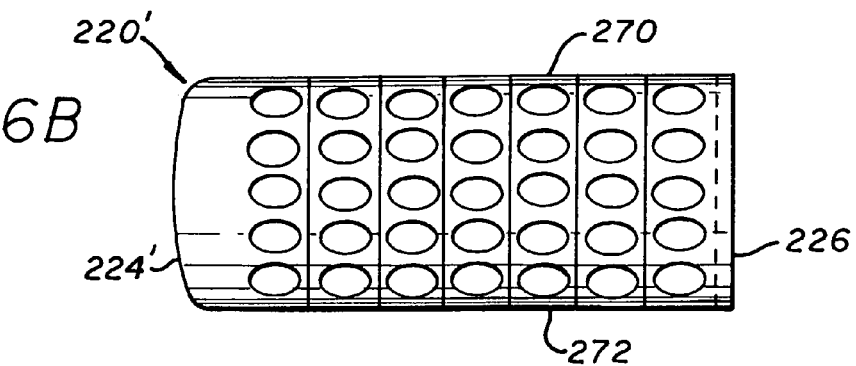
FIG. 6B is a top plan view of the spinal fusion implant shown in FIG. 6A.

Referring to FIGS. 6A and 6B, an alternative embodiment of the implant 220 is shown and generally referred to by the numeral 220'. The implant 220' is similar in configuration to implant 220 and has ratchetings 240' having a radius $R_5$ measured from the longitudinal central axis $L_5$ that increases in size from the insertion end 224' to the trailing end 226'. The ratchetings 240' each have a height measured from the body 222' that is not constant throughout the length of the implant 220'. In the preferred embodiment, the ratchet radius $R_5$ and the ratchet height increase in size from the insertion end 224' to the trailing end 226'.

As shown in FIG. 6B, the implant 220' has truncated sides 270 and 272 forming two planar surfaces which are diametrically opposite and are parallel to the longitudinal axis $L_4$. In this manner, two implants 220' may be placed side by side with one of the sides 270 or 272 of each implant touching, such that the area of contact with the bone of the adjacent vertebrae and the ratchetings 240' is maximized. Alternatively, the implant 220' may have one truncated side.

Figure 7:
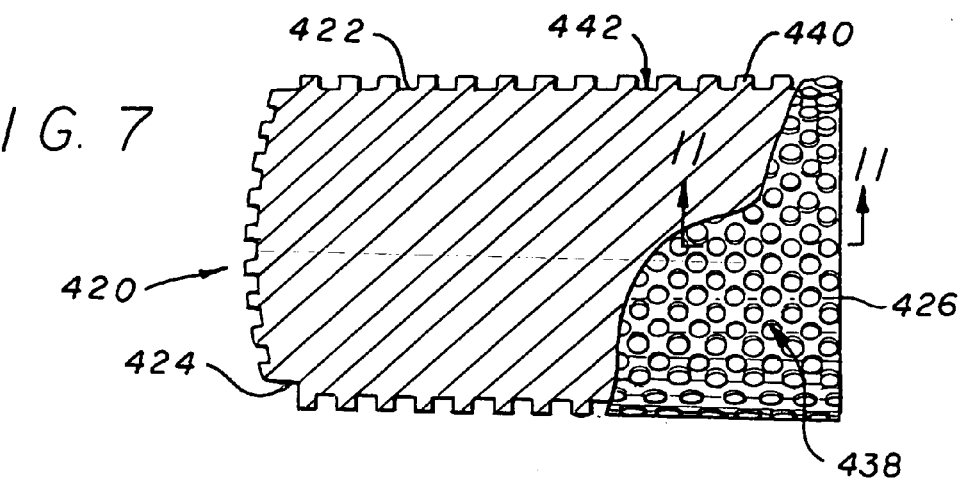
FIG. 7 is a side elevational view in partial cut-away of an alternative embodiment of the spinal fusion implant having a body that is frusto-conical and a surface configuration comprising a plurality of spaced apart posts.

Referring to FIG. 7, a side elevational view in partial cut-away of an alternative embodiment of the implant of the present invention is shown and generally referred to by the numeral 420. The implant 420 has a body 422 that is frusto-conical in shape substantially along the portion of the implant 420 that is in contact with the adjacent vertebrae of the spine and has an insertion end 424 and a trailing end 426. The implant 420 has an outer surface 438 that is capable of receiving and holding bone, or other materials capable of participating in the fusion process and/or capable of promoting bone ingrowth. In the preferred embodiment, the surface 438 comprises a plurality of posts 440 that are spaced apart to provide a plurality of interstices 442 which are partial wells with incomplete walls capable of holding and retaining milled bone material or any artificial bone ingrowth promoting material. The implant 420 may be prepared for implantation by grouting or otherwise coating the surface 438 with the appropriate fusion promoting substances.

Figure 8:
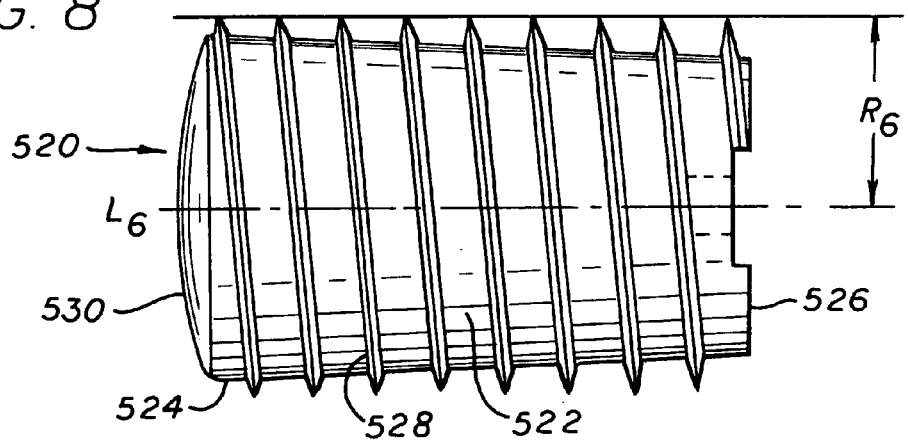
FIG. 8 is a side elevational view of an alternative embodiment of the spinal fusion implant of FIG. 1.

Referring to FIG. 8, a side elevational view of an alternative embodiment of the spinal fusion implant of the present invention generally referred to by numeral 520 is shown. The implant 520 has a body 522 having a root diameter that is frusto-conical in the reverse direction as that of implant 20 shown in FIG. 1, in order to preserve and/or restore lordosis in a segment of spinal column when inserted from the posterior aspect of the spine. The body 522 has an insertion end 524 and a trailing end 526. In the preferred embodiment, the body 522 of the implant 520 has a minimum diameter at a point nearest to the trailing end 526 and a maximum diameter at a point nearest to the insertion end 524. The insertion end 524 may have an anterior nose cone portion 530 presenting a tapered end to facilitate insertion.

The implant 520 has an external thread 528 having a substantially uniform radius $R_6$ measured from the central longitudinal axis $L_6$ of the implant 520, such that the external diameter of the external thread 528 (major diameter) has an overall configuration that is substantially parallel to the longitudinal axis $L_6$. It is appreciated that the thread 528 can have a major diameter that varies with respect to the longitudinal axis $L_6$, such that the major diameter may increase from the insertion end 524 to the trailing end 526 or the reverse. The external thread 528 has a thread height measured from the body 522 that increases from the insertion end 524 to the trailing end 526.

Figure 9:
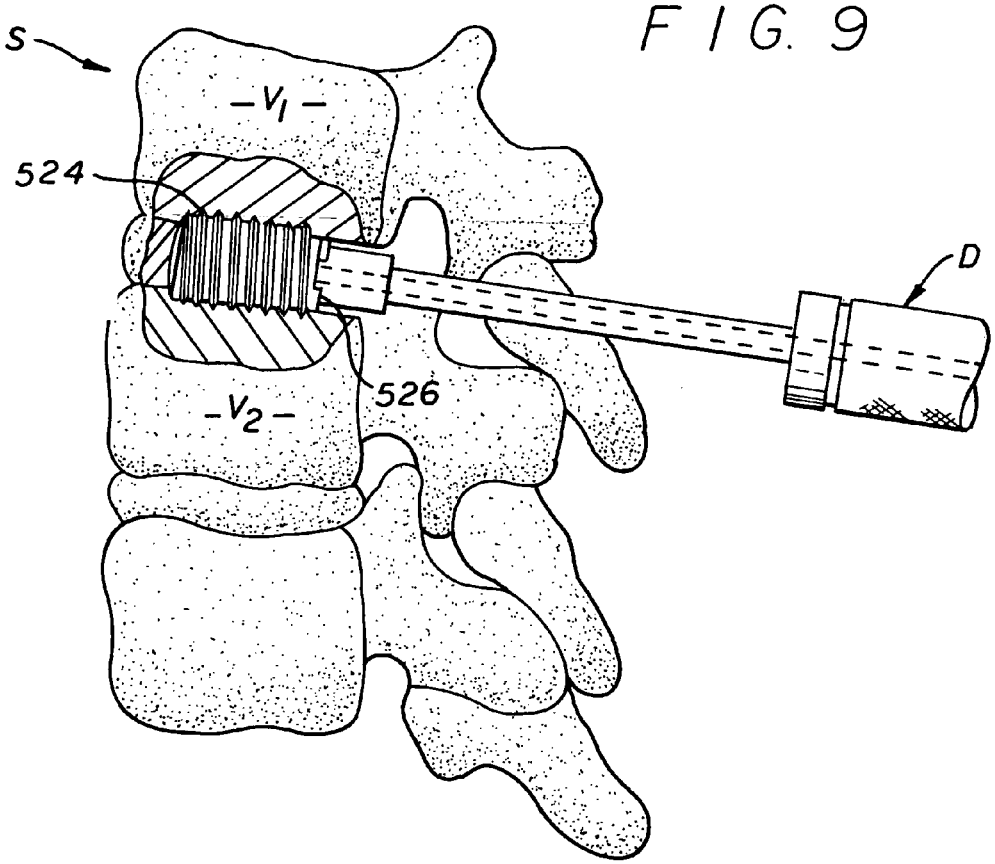
FIG. 9 is a side elevational view and partial cut-away of a segment of the spinal column in lordosis showing the spinal fusion implant of FIG. 8 being implanted with a driving instrument from the posterior approach to the spinal column.

Referring to FIG. 9, a segment of the spinal column S is shown with the vertebrae $V_1$ and $V_2$ in lordosis and an implant 520 shown being inserted from the posterior aspect of the spinal column S with an instrument driver D. The implant 520 is inserted with the larger diameter insertion end 524 first in order to in initially distract apart the vertebrae $V_1$ and $V_2$ which then angle toward each other posteriorly as the implant 520 is fully inserted. It is appreciated that the insertion of implant 520 does not require the adjacent vertebrae $V_1$ and $V_2$ to be placed in lordosis prior to insertion, as the full insertion of the implant 520 itself is capable of creating the desired lordotic angular relationship of the two vertebrae $V_1$ and $V_2$.

In the preferred embodiment of implant 520, for use in said lumbar spine, the implant 520 has an overall length in the range of approximately 24 mm to 30 mm, with 26 mm being the preferred length. The body 522 of the implant 520 has a root diameter at the insertion end 524 in the range of 12–22 mm, with 16 mm being the preferred root diameter at the insertion end, and a root diameter at the trailing end 526 in the range of 10–20 mm, with 14 mm being the preferred diameter at the trailing end 526. In the preferred embodiment, the imp 520 has a thread radius $R_6$ in the range of 6 mm to 12 mm, with 8 mm being the preferred radius $R_6$.

Figure 10:
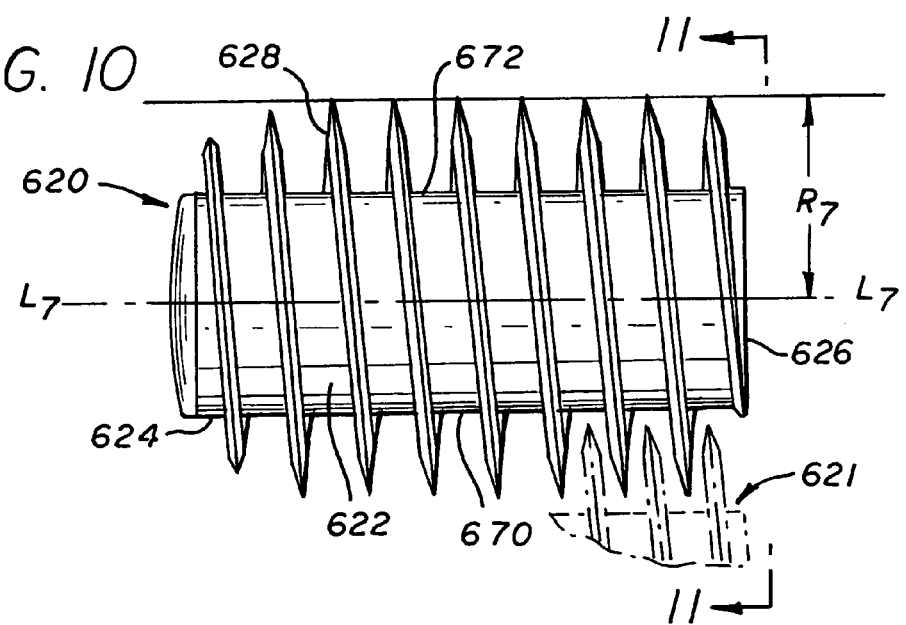
FIG. 10 is a side elevational view of an alternative embodiment of the spinal fusion implant having a frusto-conical body and truncated sides.

Referring to FIG. 10, an alternative embodiment of the spinal fusion implant of the present invention generally referred to by the numeral 620 and a partial fragmentary view of a second identical implant, generally referred to by the numeral 621 are shown. The implant 620 has a body 622 that is partially frusto-conical in shape similar to body 22 of implant 20 shown in FIG. 1, and has an insertion end 624 and a trailing end 626. The body 622 of the implant 620 has truncated sides 670 and 672 forming planar surfaces that are parallel to the longitudinal axis $L_7$. In this manner, two implants 620 and 621 may be placed side by side, with one of the sides 670 or 672 of each implant with little space between them, such that the area of contact with the bone of the adjacent vertebrae is maximized. It is appreciated that the body 622 may also be cylindrical in shape and have truncated sides 670 and 672.

The implant 620 has an external thread 628 having a radius $R_6$ measured from the central longitudinal axis $L_7$ that may be constant, such that the major diameter or outer locus of the external thread 628 has an overall configuration that is substantially cylindrical. It is appreciated that the external thread 628 may have a thread radius $R_7$ that is variable with respect to the longitudinal axis $L_7$ such that the major diameter or outer locus of the external thread 628 has an overall configuration that is substantially frusto-conical.

Figure 11:
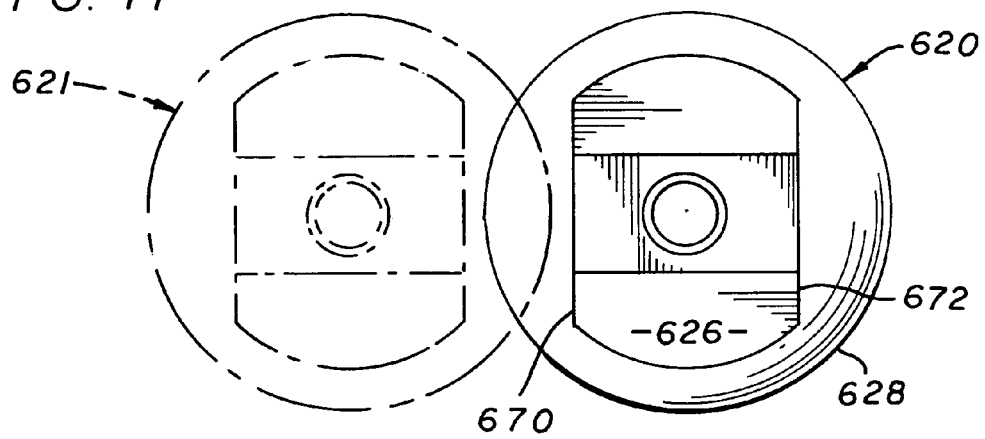
FIG. 11 is an end view along line 11—11 of the spinal fusion implant of FIG. 14 shown placed beside a second identical implant shown in hidden line.

Referring to FIG. 11, an end view of the implant 620 placed beside implant 621 is shown. The implant 620 has a thread radius that is substantially constant and has a thread height measured from the body 622 that is greater at the sides 670 and 672. In this manner, two implants 620 and 621 can be placed beside each other with the external thread 628 of each implant interdigitated allowing for closer adjacent placement of the two implants as a result of the substantial overlap of the external thread 628 at the side 670 or 672 of the implants.

Figure 12:
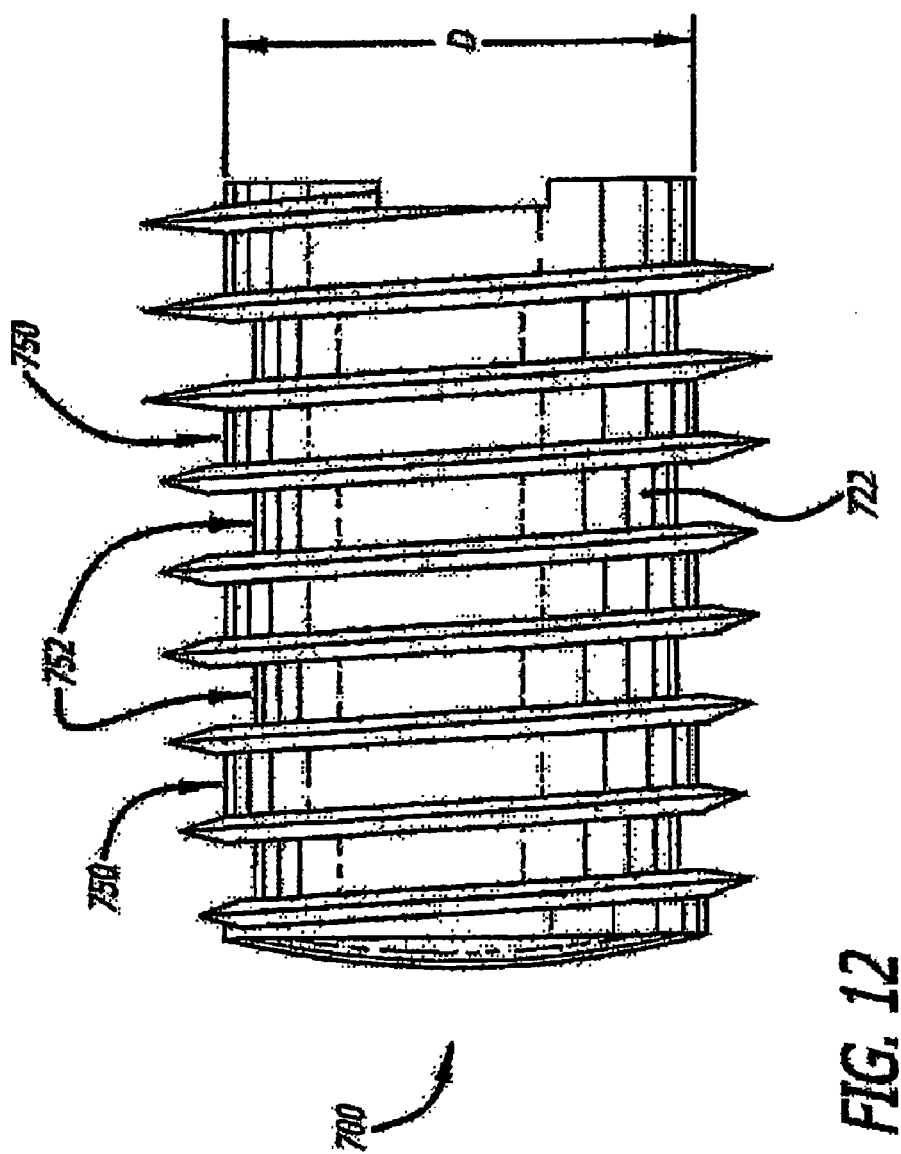
FIG. 12 is a side elevational view of an alternative embodiment of the spinal fusion implant having a body with an irregular configuration.

Referring to FIG. 12, an alternative embodiment of the implant of the present invention is shown and generally referred to by the numeral 700. The implant 700 is similar in configuration to implant 20 shown in FIG. 1, except that the body 722 has an irregular configuration. The configuration of the body 722 has a root diameter D which is variable in size throughout the length of the implant 700 and, as shown in this embodiment, comprises larger diameter portions 750 and smaller diameter portions 752. It is appreciated that each of the large diameter portions 750 may be of the same or different diameter and each of the smaller diameter portions 752 may be of the same or different diameter.

The outer surface of the body 722 of implant 720 may be filled with fusion promoting substances such that the smaller diameter portions 752 may hold such fusion promoting substances. If so filled, the composite of the implant 700 and the fusion promoting material could still produce an even external surface of the body 722 if so desired.

THE METHOD OF THE PRESENT INVENTION

The embodiments of the frusto-conical implants of the present invention described above may be implanted with the method of the present invention described below.

In the preferred method of the present invention, the diseased disc between two vertebrae is at least partially removed from the anterior aspect of the spine. The two vertebrae adjacent the diseased disc are then optimally distracted and placed in the desired amount of lordosis by any of a number of well known means including, but not limited to, those means that distract the vertebral bodies by engaging screws placed into the anterior aspect of the vertebral bodies, and disc space distractors that are placed from the anterior aspect of the spine into the disc space and are then used to urge the vertebral endplates away from each other and into lordosis. When the correct amount of distraction and lordosis have been achieved at the affected disc level, then a frusto-conical space is created from anterior to posterior between the adjacent vertebrae. The frusto-conical space that is created is greater in diameter than the disc space height, such that some bone is removed from each of the adjacent vertebrae. The created space is generally frusto-conical in shape, being greatest in diameter anteriorly and tapering to a lesser diameter posteriorly.

It should be noted that where the spine is of sufficient width, it may be possible to prepare two such frusto-conical spaces side-by-side at the same disc level, allowing for the use of two implants instead of one. In either event, once the frusto-conical space is prepared and all debris removed, the implant is then inserted into the prepared space across the disc space, penetrating into each of the adjacent vertebrae, from anterior to posterior.

In the preferred embodiment, the diseased disc is first removed by conventional discectomy. The depth of the disc space is then determined by direct measurement. An interspace distractor such as that described by Michelson in U.S. Pat. No. 6,080,155, incorporated herein by reference, is then inserted into the disc space. A series of such distractors are available and are sequentially inserted until the optimal amount of distraction across the disc space is achieved. The interspace distractors utilized for this purpose are wedged so as to induce physiological lordosis.

Figure 16:
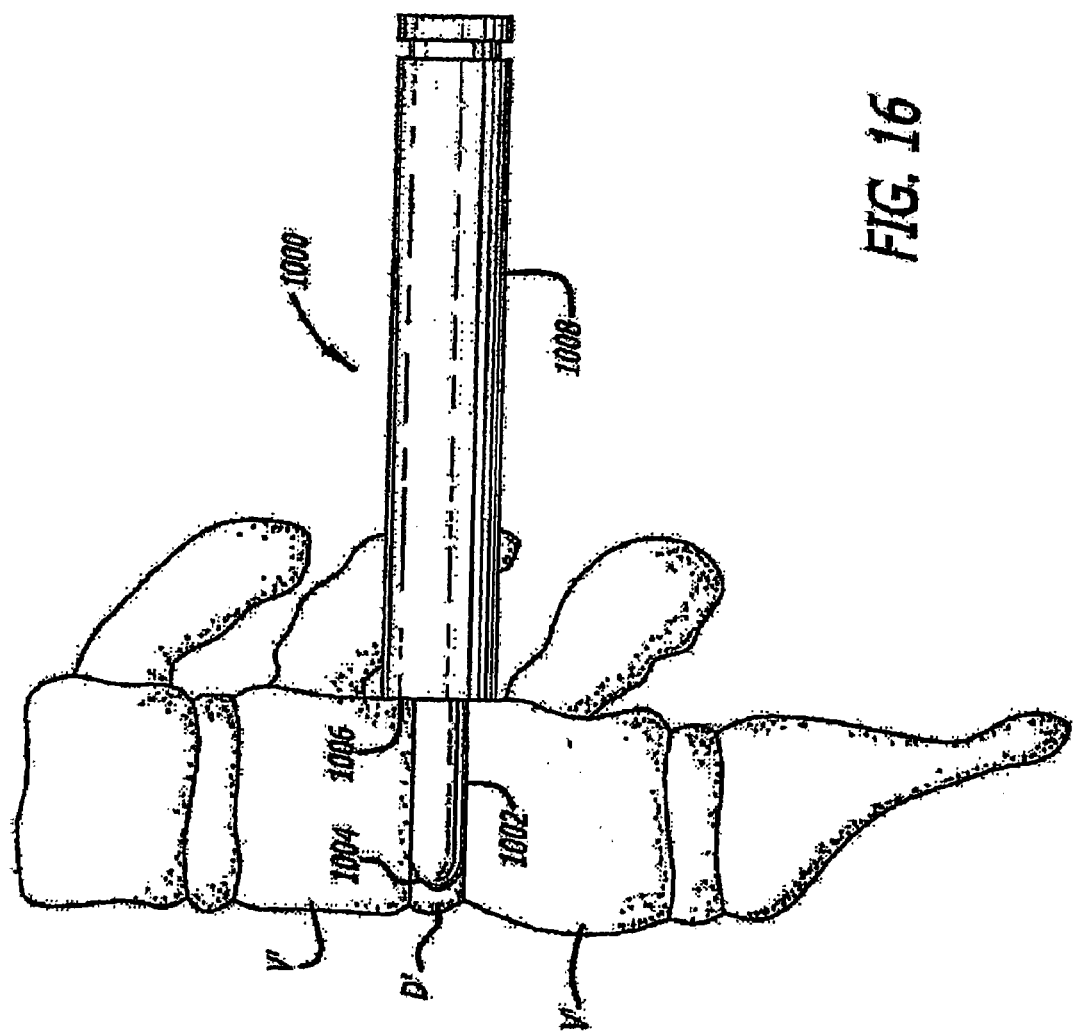
FIG. 16 is a side elevational view of a long distractor inserted into an intervertebral space.

For example, referring now to FIG. 16, preferably after removing some portion of nuclear disc material, a disc penetrating portion 1002 of a long distractor 1000 is inserted under direct vision into the intervertebral (or disc) space and disc D'between the vertebral bodies V'. The penetrating portion 1002 is essentially cylindrical with a bullet-shaped front end 1004 and a shoulder portion 1006 where the penetrating portion 1002 extends from barrel 1008. The penetrating portion 1002 urges the vertebral bodies apart, facilitating the introduction of the instruments. Long distractors with sequentially increasing diameter penetrating portions 1002 are then introduced. As the optimal diameter of penetrating portion 1002 is achieved, the vertebrae V' to either side are forced into full congruence and thus become parallel, not only to the penetrating portion 1002, but to each other.

Figure 17:
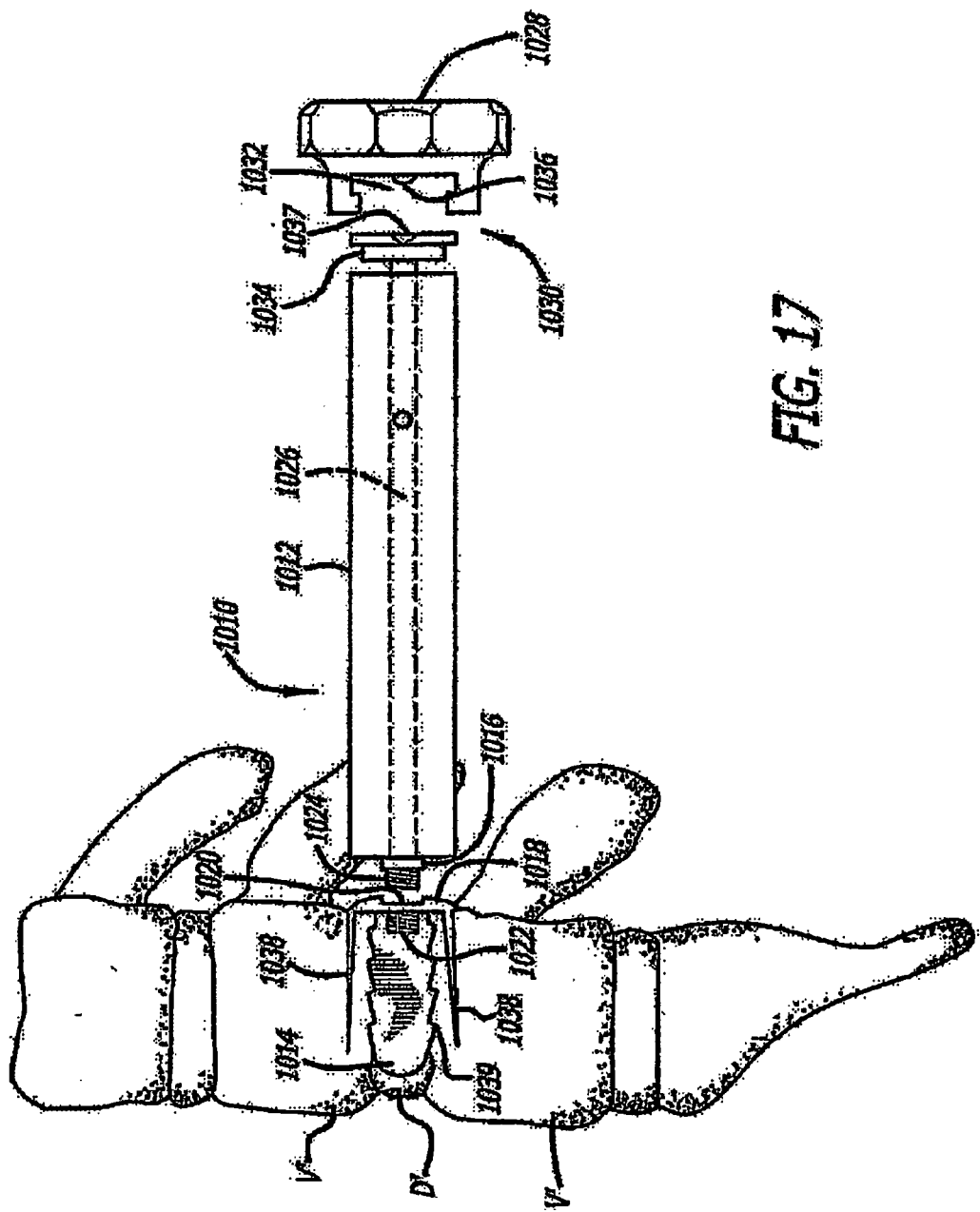
FIG. 17 is a side elevational view of a convertible long distractor including a short distractor positioned in the intervertebral space.

Referring to FIG. 17, in the preferred embodiment, a convertible long distractor 1010 is used on the first side of the spine. The convertible long distractor 1010 has a barrel portion 1012 separable from a short distractor 1014. While the initial distraction may be performed with a solid long distractor, as the optimal distraction is approached the appropriate convertible long distractor is utilized. The barrel portion 1012 includes a rectangular projection (or male mating member) 1016 at one end, and the short distractor 1014 has an increased diameter head 1018, a female rectangular slot 1020 and an internal threaded opening 1022.

The short distractor 1014 is removably attached to the barrel portion 1012 via the mating of female rectangular slot 1020 and the male mating member 1016. The mating of the female rectangular slot 1020 and the male mating member 1016 is held together by threading a threaded working end screw 1024 of an interior shaft 1026 extending through the barrel portion 1012 into the female rectangular slot 1020. The threaded working end screw 1024 corresponds to the internal threaded opening 1022. A knob 1028 serves to drive a crown 1030 connected to the interior shaft 1026. The knob 1028 has a open socket 1032 for fitting around the crown 1030, and engages a reduced diameter hexagonal portion 1034 of the crown 1030 to rotate the interior shaft 1026 and the threaded working end screw 1024. A detent ball 1036 on the inside of the open socket 1032 engages a detent 1037 in the crown 1030 to hold the knob 1028 and the crown 1030 together.

Figure 18:
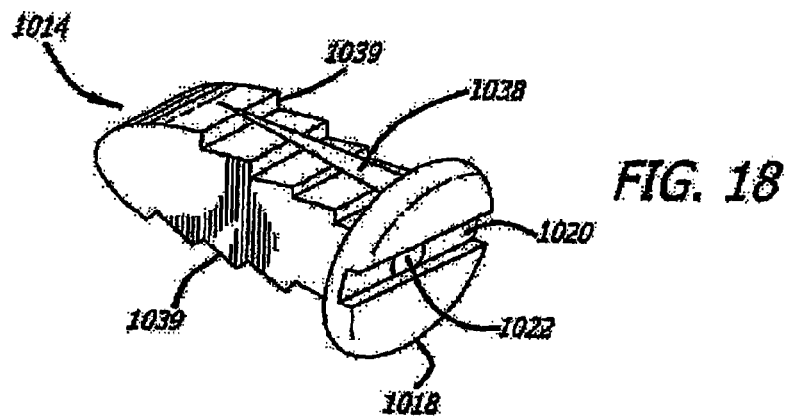
FIG. 18 is a perspective view of the short distractor shown in FIG. 17.
Figure 18A:
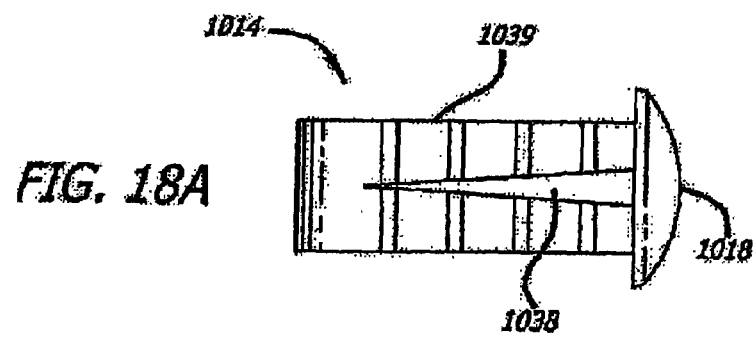
FIG. 18A is a side elevational view of the short distractor shown FIGS. 17 and 18.
Figure 18B:
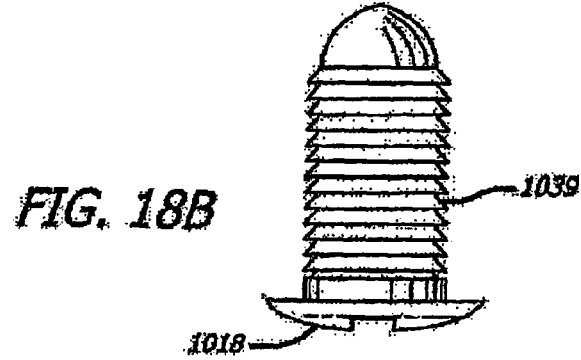
FIG. 18B is a side elevational view of an alternative short distractor with circumferential forward facing ratchetings.
Figure 18C:
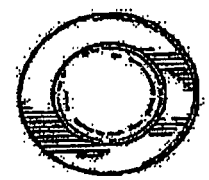
FIG. 18C is a top view of the alternative short distractor of FIG. 18B.
Figure 18D:
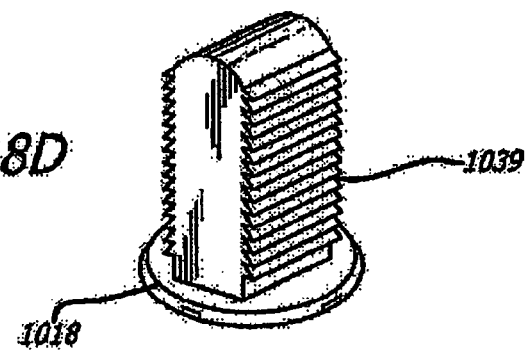
FIG. 18D is a perspective view of an another alternative short distractor.
Figure 18E:
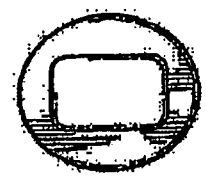
FIG. 18E is a top view of the alternative short distractor of FIG. 18D.
Figure 18F:
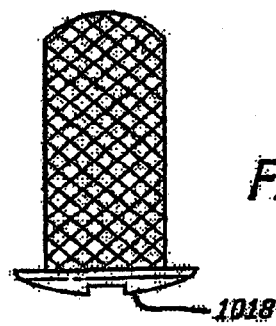
FIG. 18F is a side elevational view of a further alternative short distractor having knurled surfaces.

Referring to FIGS. 17, 18, and 18A-18F the short distractor 1014 shown therein are designed to provide for high stability when temporarily situated so as to resist inadvertent migration while the surgeon is working on the second side. To that end, the embodiment of the short distractor 1014 shown in FIGS. 17, 18, and 18A, has a pair of sharp pegs (or prongs) 1038, to embed into the opposing vertebral bodies and forward facing ratchetings 1039, that further resist backward movement. FIGS. 18B and 18C are side and top views of an alternative embodiment of the a short distractor 1014 such that the distractor portion to be interposed between the vertebrae is essentially cylindrical, but with circumferential forward facing ratchetings 1039. Referring to FIGS. 18D and 18E, another alternative embodiment of the short distractor 1014 is shown having a more rectangularized design, with forward facing ratchetings, without the sharp prongs 1038 of FIGS. 17, 18, and 18A. FIG. 18F is a side view of a further alternative embodiment of the short distractor 1014 shown with knurling, to increase the interference with the bone surface so as to add stability to the unit and to resist dislodgment. To this end, it is apparent that the working ends of both the long and short distractors can have a variety of configurations consistent with their purpose, and that surface irregularities as well as the shape of the ends themselves, with or without prongs 1038, may be utilized to make the short distractor 1014 more resistant to migration.

Figure 19:
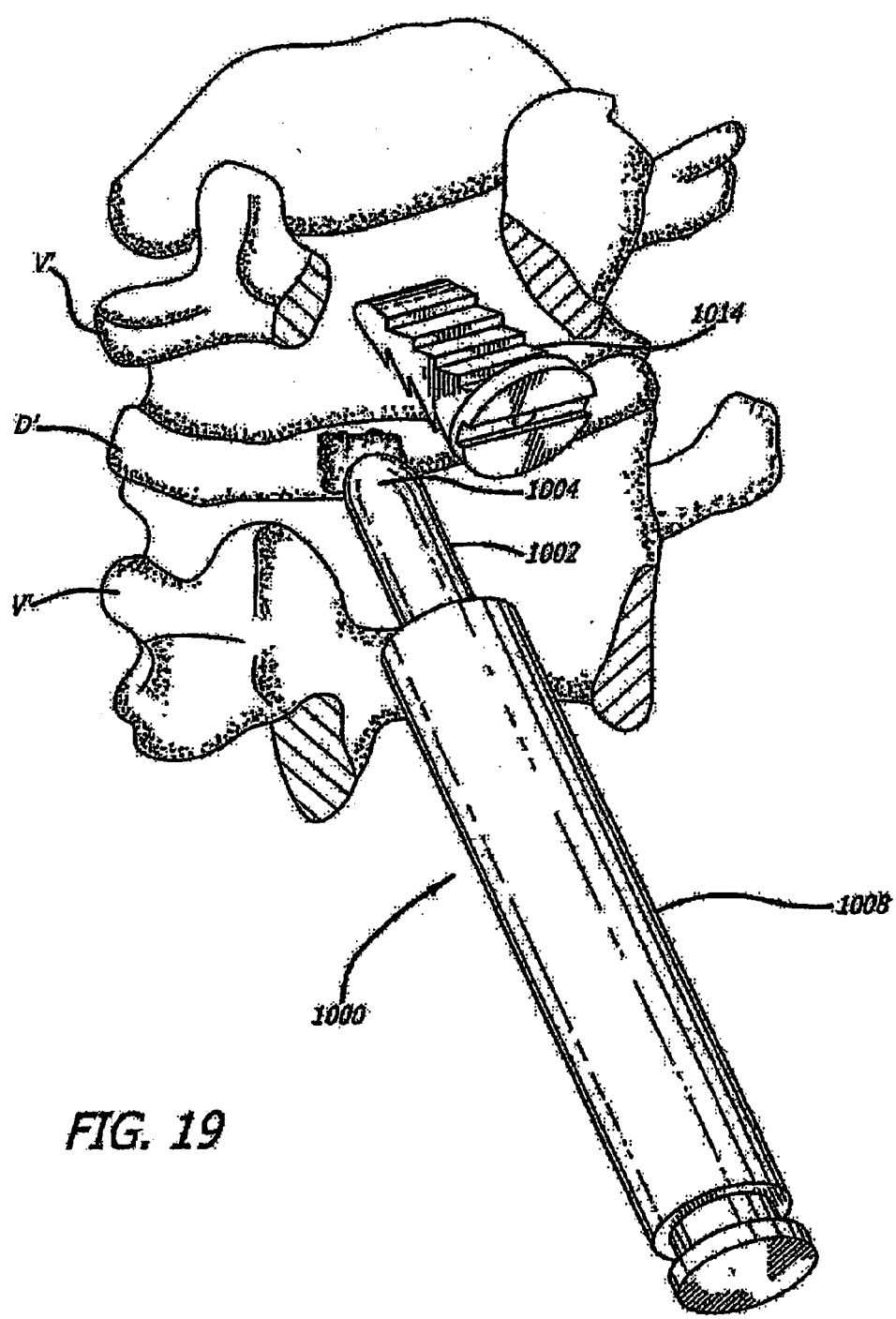
FIG. 19 is a perspective view of a spinal segment (two vertebrae and an interposed disc) with a short distractor in place, with a portion of the upper vertebrae and disc cut away to show the short distractor on one side of the spine and a long distractor about to be placed contralaterally.

Once the ideal distraction has been achieved on the first side of the spine, the convertible distractor 1010 is dissociated, leaving the short distractor 1014 in place. Referring to FIG. 19, the surgeon then moves to the other side of the spine at the same disc level, and retracts the dural sac and nerve root medially, exposing the disc on that side. Long distractors 1000 are then sequentially inserted into the disc space until the diameter of the distractor on the second side is at least as big as that on the first side. Although use of long distractor 1000 and convertible distractor 1010 are shown in FIGS. 16, 17, and 18 being used posteriorly, similar devices can be used anteriorly.

An outer sleeve is then fitted over the barrel portion of the interspace distractor barrel 1008 of long distractor 1000 or barrel 1012 of convertible distractor 1010 and firmly seated in engagement with the spine. As discussed below and previously described in U.S. Pat. No. 6,080,155, the outer sleeve may itself have extended portions capable of either maintaining or of obtaining and maintaining distraction. The outer sleeve may also have vertebrae engaging prongs to further stabilize the outer sleeve to the spine and to more rigidly control motion at the adjacent vertebrae. As discussed below and described in U.S. Pat. No. 6,080,155, the use of the extended outer sleeve with distractor portions actually makes it possible to achieve the optimal distraction and lordosis without the use of the described interspace distractor. A number of different embodiments of outer sleeves are discussed below. However, if the interspace distractor is used, then the outer sleeve is fully engaged to the spine, the distractor is removed, and in the preferred method by use of a slap-hammer, engaging the most proximal aspect of the distractor.

Figure 20:
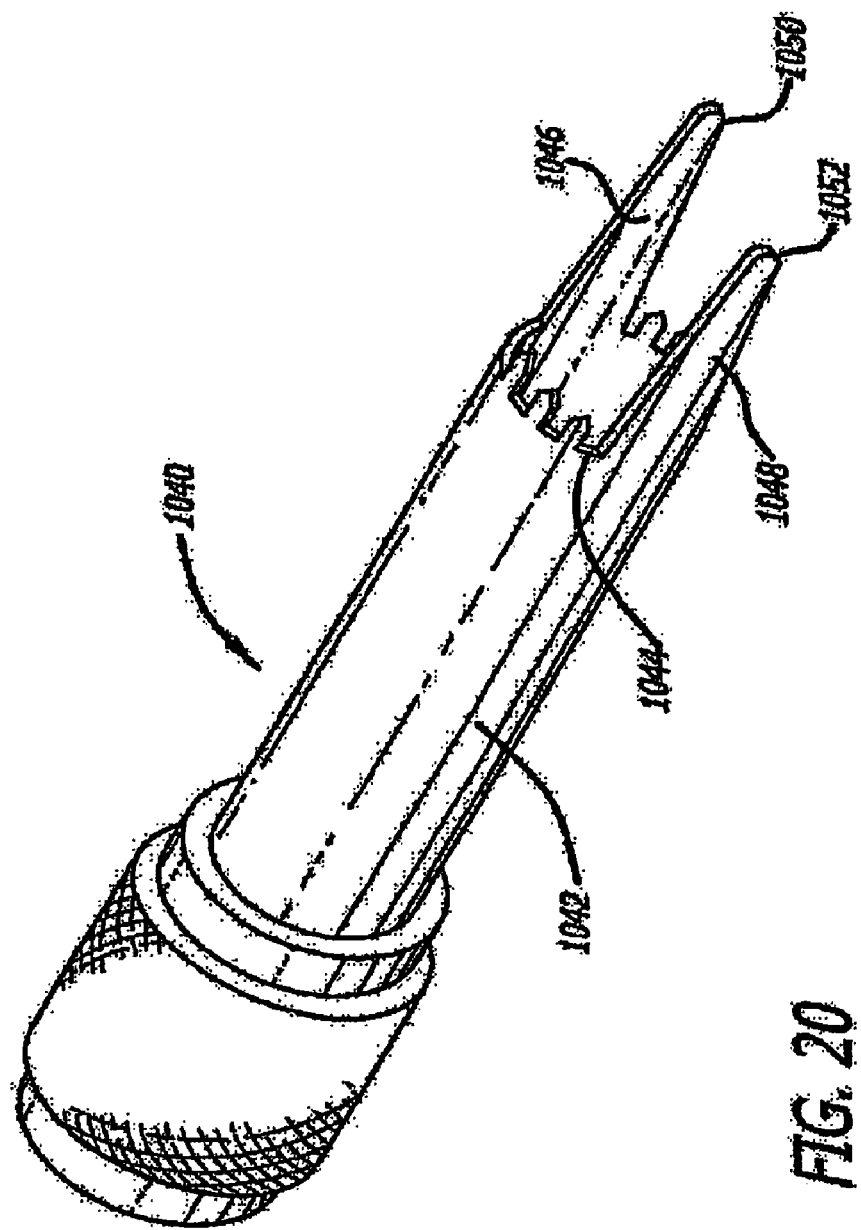
FIG. 20 is a perspective view of an anterior lordotic extended outer sleeve having extended members for restoring and maintaining lordosis of the spine from the anterior aspect of the spine.

For example, referring to FIG. 20, an anterior extended outer sleeve 1040 for use from the anterior approach of the spine is shown. The anterior extended outer sleeve 1040 comprises a hollow tubular member 1042 having a distal end 1044 which has been extended such that a pair of extended portions 1046 and 1048 which are essentially a continuation of the tubular member 1042 and are opposed 180 degrees from each other. The extended portions 1046 and 1048 are configured to restore and maintain lordosis of the spine from the anterior approach. The extended portions 1046 and 1048 each have a height that is greater at a point proximate to the distal end 1044 of the tubular member 1042 that decreases in the direction away from the tubular member 1042. The extended portions 1046 and 1048 are tapered at their leading edges 1050 and 1052, respectively, to facilitate insertion into the disc space.

Figure 21:
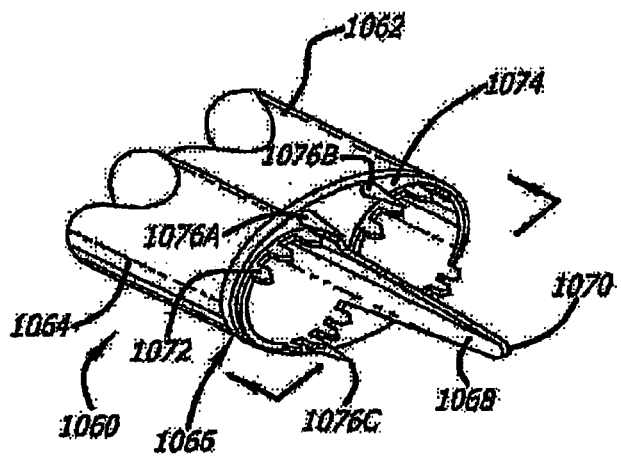
FIG. 21 is a perspective view of a dual extended outer sleeve having an extension that decreases in height in the direction of insertion.
Figure 22:
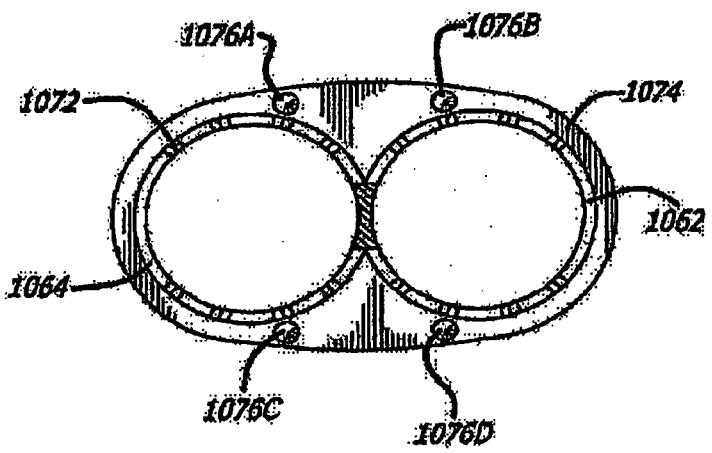
FIG. 22 is a front elevational view of the dual extended outer sleeve shown in FIG. 21.

While the anterior extended outer sleeve 1040 for use anteriorly is shown in the singular form and in use in the lumbar spine, it is understood that it may take a double barrelled form and in either form, be used throughout the spine. For example, referring to Figures 21 and 22, a dual extended outer sleeve is shown and generally referred to by the numeral 1060. The dual extended outer sleeve 1060 comprises two hollow tubular members 1062 and 1064. The two hollow tubular members 1062 and 1064 have a distal end 1066 which has been extended to form an extended portion 1068 which is essentially a continuation of the hollow tubular members 1062 and 1064 joined together. The extended portion 1068 is similar in shape and function to the extended portions 1046 and 1048 described above in reference to FIG. 20. The extended portion 1068 has a height that is greater at a point proximate the distal end 1066 and decreases in the direction away from the hollow members 1062 and 1064, in order to maintain the normal curvature of the spine by correcting the angular relationships of the vertebrae V'. The extended portion 1068, is tapered at its leading edge 1070 to facilitate insertion of the extended portion 1068 into the disc space between two adjacent vertebrae V'. Located at the distal end of the tubular members 1062 and 1064 are sharpened teeth 1072 for engaging the vertebrae V'. The tubular members 1062 and 1064 may be bridged in part or wholly throughout their length, but are typically fixed by a foot plate 1074. Referring specifically to FIG. 22, the foot plate 1074 has an oval configuration that contours and hugs the vertebrae V' and has a plurality of prongs 1076A-1076D extending from the foot plate 1074 is shown. The prongs 1076A-1076D are sufficiently long to engage the bone of adjacent vertebrae V', but limited in length so as not to over penetrate beyond the vertebrae once inserted.

Figure 23:
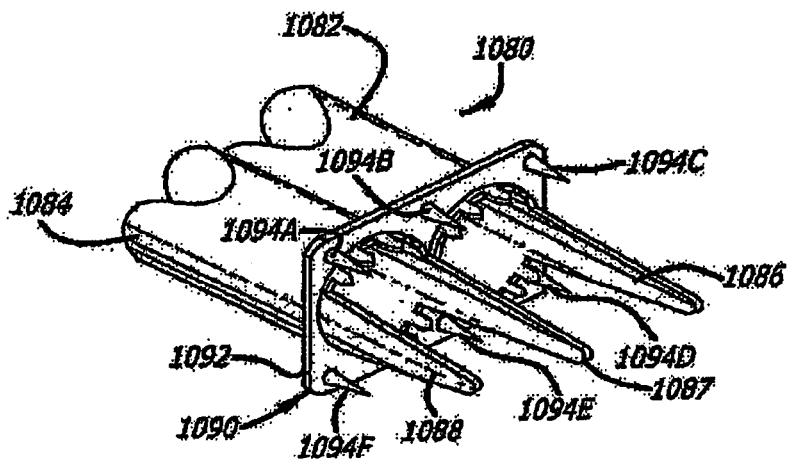
FIG. 23 is a perspective view of a dual extended outer sleeve having two extensions that decrease in height in the direction insertion.

Referring to FIG. 23, another dual extended outer sleeve 1080 having two hollow tubular members 1082 and 1084 is shown. The dual extended outer sleeve 1080 is similar to the dual extended outer sleeve 1060, except that it has additional extended portions 1086, 1087 and 1088 which have a height that is greater near the distal end 1090 of the hollow tubular members 1082 and 1084 and decreases in the direction away from the hollow tubular members 1082 and 1084. The extended portions 1086, 1087 and 1088 are similar in shape and function to the extended portions 1046 and 1048 described above in reference to FIG. 20. A foot plate 1092 is also provided. As the foot plate 1092 is rectangular and larger than foot plate 1074, prongs 1094E and 1094F, in addition to prongs 1094-1094D, may be added.

Figure 13:
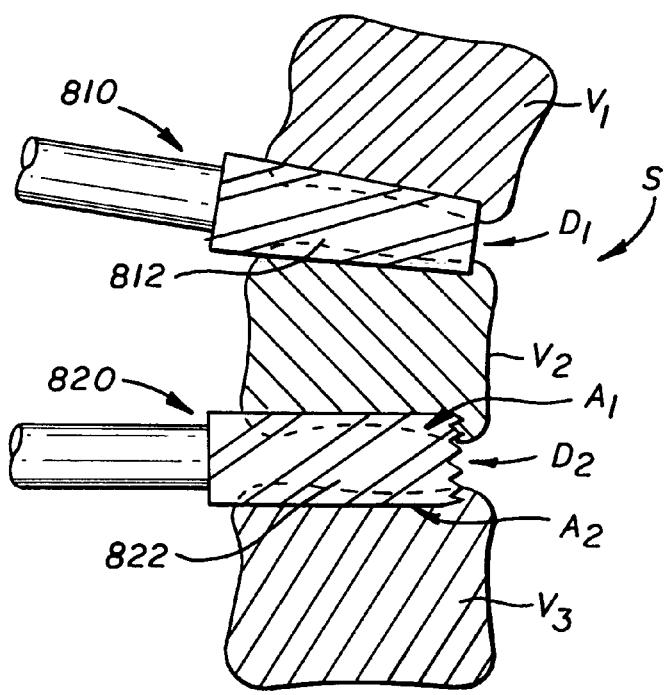
FIG. 13 is a side elevational view of a segment of the spinal column partially in lordosis showing a first drill and a second drill used in the method of the present invention.

Referring to FIG. 13, a segment of the spinal column S is shown with vertebrae $V_1$ and $V_2$ shown in lordosis adjacent to disc space $D_1$ and vertebrae $V_2$ and $V_3$ shown not in lordosis, but relatively parallel to each other adjacent disc space $D_2$. A first drill 810 making an opening 812 across the disc space $D_1$, and into adjacent vertebrae $V_1$ and $V_2$, and a second drill 820 making an opening 822 across the disc space $D_2$ and into adjacent vertebrae $V_2$ and $V_3$ are shown in FIG. 13. In the preferred embodiment, the interbody spinal fusion implant itself is threaded and frusto-conical in shape and therefore, the remaining portion of the procedure will be described in regard to that particular embodiment of the present invention, by way of example. With the disc space fully distracted and in anatomical lordosis and with the outer sleeve firmly engaged to the spine, it is then desirable to prepare the spine for receipt of the interbody fusion implant. It is preferable to prepare a space across the disc space and penetrating into the adjacent vertebrae which space corresponds roughly to the root dimensions of the implant to be implanted. For this purpose, a stopped-out bone cutting instrument is inserted through the outer sleeve, the shape of the cutting portion of the first drill 810 generally corresponding to the frusto-conical shape of the root diameter of the implant being inserted. This instrument may take the form of a frusto-conical drill or a mill and may be used to cut the bone by rotation, said rotation being achieved either through a manual handle or with power. Having prepared the space, the surgeon has two options. One is to remove the outer sleeve and then, because the implant is itself frusto-conical, screw the implant in using an implant driver capable of locking to the implant. The other is to leave the outer sleeve in place during the insertion of the implant.

If per the above, the surgeon wishes to remove the outer sleeve, the insertion of the implant itself causes a reproduction of the previous distraction which is easily achieved as the implant itself is frusto-conical in shape and the space created by the removal of the bone to either side of the disc space essentially corresponds to the root diameter of the implant such that as the implant is inserted, the threads are embedded into the vertebrae adjacent the disc space. Once the implant is fully inserted, the insertion apparatus is disconnected from the implant. If the cervical disc space is sufficiently wide from side-to-side, the procedure is performed in the same manner except that either a double-barreled outer sleeve may be used or the previously described procedure essentially performed twice at the same disc level, such that a pair of implants may be inserted side-by-side.

In the alternative, if the surgeon wishes to leave the outer sleeve in place during the insertion of the implant and if the implant, as per this example has both a minor and a major diameter such as with a threaded implant, then the bone removing portion of the drilling means needs to generally correspond to the root diameter of the implant while the inside diameter of the outer sleeve needs to be great enough to allow the passage of the major diameter of the implant. It is desirable to stabilize the bone removal instrument and to assure that it removes equal portions of bone from each of the adjacent vertebrae. This may be achieved by a reduction sleeve which fits between the bone removal means and the inner wall of the outer sleeve and which essentially corresponds to the difference between the minor and major diameters of the implant, or some portion of the drill shaft proximal to the cutting end may have a diameter which corresponds to the major diameter of the implant even while the distal bone removing portion corresponds to the root diameter of the implant. In either way, the bone removal instrument is both stabilized and centered within the outer sleeve.

The approach to the lumbar spine may either be retroperitoneal, or transperitoneal. The procedure may be performed under direct vision, or laproscopically with the use of an endoscope. Generally it is preferable to utilize two implants which are inserted in an anterior to posterior direction, one to either side of the midline. The implants may be inserted using either a single-barreled or double-barreled outer sleeve as described above, and by the methods previously described U.S. Pat. No. 6,080,155 from which the present methods differ only in the shape of the drill end or bone milling device which is essentially conical. As also previously described, in U.S. Pat. No. 6,080,155, the methods can be utilized for the insertion of non-threaded implants (such as implants 222') in which case the implants are linearly advanced rather than threaded in. And finally, as previously described in U.S. application Ser. No. 08/390,131, now U.S. Pat. No. 5,593,409, the implants themselves may have truncations on the sides to form a planar surface parallel to the longitudinal axis of the implant, such that it is possible to fit two such implants more closely together by narrowing the width of each while preserving their height. As taught in U.S. Pat. No. 6,080,155, a tap may be used after the drilling step and prior to the insertion of the implants.

Figure 25:
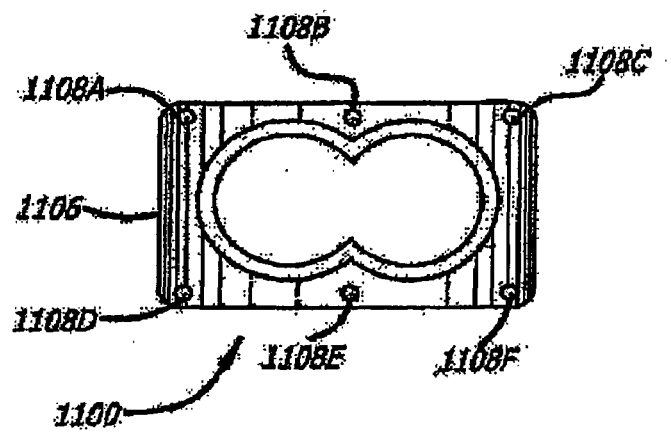
FIG. 25 is a front elevational view of the dual extended outer sleeve shown in FIG. 24.
Figure 24:
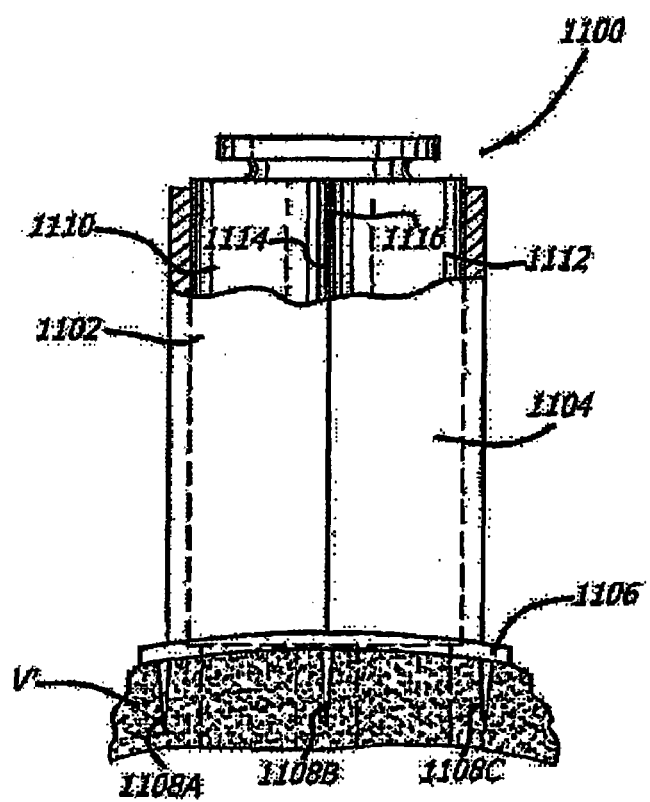
FIG. 24 is top plan view of a dual extended outer sleeve for use in installing interbody spinal implants having one or more flat sides, shown placed over two long distractors with the prongs inserted into a vertebrae.
Figure 26:
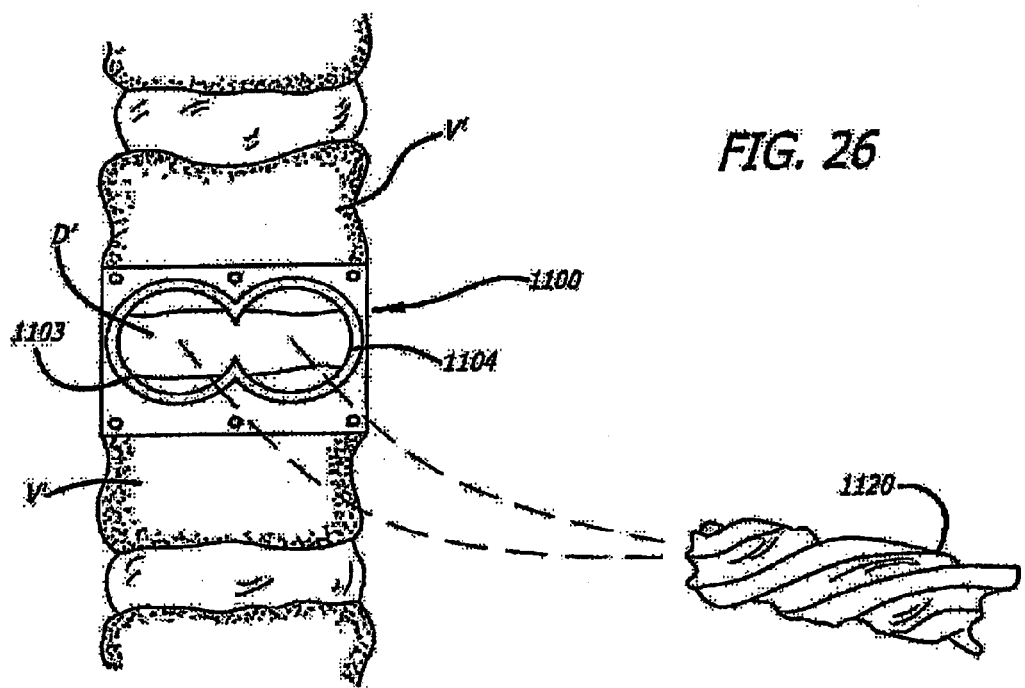
FIG. 26 is a rear elevational view of the dual extended outer sleeve of FIG. 24 positioned relative a disc space to receive a drill therein.

For example, when implants having truncated sides, such as two implants 220' shown in FIGS. 6A and 6B, a dual outer sleeve 1100 having a pair of overlapping, hollow cylindrical tubes 1102 and 1104 can be utilized as shown in FIGS. 24-26. The cylindrical tubes 1102 and 1104 are identical in size and each has an internal diameter slightly larger than the outer diameter of the spinal fusion implant to be inserted therethrough. The cylindrical tubes 1102 and 1104 are in communication with each other along their length and are displaced from each other ideally a distance that is slightly greater than the sum of the diameters of two spinal fusion implants 220' placed side-by-side with the flat sides 270 of each of the spinal fusion implants touching. The cylindrical tubes 1102 and 1104 are joined longitudinally such that they are partially overlapping. The cylindrical tubes 1102 and 1104 are mounted on a foot plate 1106 similar to the foot plate 1092 shown in FIG. 23. There are a series of prongs 1108A-1108F projecting from the foot plate 1106 which are used to engage the dual outer sleeve 1100 to the base of the adjacent vertebrae V'.

Referring specifically to FIG. 24, the dual outer sleeve 1100 is introduced over two long distractors 1110 and 1112 placed side-by-side and protruding anteriorly from the vertebrae V'. The long distractors 1110 and 1112 are similar to the long distractor 1000 described above except that they have a flat side 1114 and 1116 respectively.

As shown In FIGS. 24, the foot plate 1106 is contoured so as to approximate the external curvature of the vertebrae V'anteriorly. The sharp prongs 1108A-1108F are sufficiently long to permit fixation of the foot plate 1106, but are limited in length so as to not penetrate the vertebrae V' too far posteriorly and number from 2 to 10, but preferably 6. Once the dual outer sleeve 110 has been fully seated, the vertebrae V' adjacent the disc space to be fused are rigidly held via foot plate 1106 and the prongs 1108A-1108F. Thus, it is possible to remove either one, or if desired, both of the long distractors 1110 and 1112. The dual outer sleeve has been described above for inserting two implants each having at least one flat side, and may have extended portions for insertion into the disc space which are capable of producing distraction as well as lordosis as previously described with such extensions extending in line with the lateral walls of the cylindrical tubes.

Referring to FIG. 26, once the dual outer sleeve 1100 has been fully seated, one of the long distractors 1110 and 1112 is removed and the surgeon may drill the disc space D' between the vertebrae V' utilizing drill 1120 using each of the hollow cylindrical tubes 1102 and 1104 to guide the drill 1120 in order to create overlapping holes in which the spinal fusion implants 220' may be inserted. Further, the removal of disc and bone may be accomplished by the use of a burr, or a chisel of appropriate shape for that purpose and with or without the use of a drill. Once the disc space D' has been drilled, an implant driver instrument is used to insert the spinal fusion implants 220' preferably by linear advancement. The implant driver instrument may be used to either insert or to remove the spinal fusion implants 220'.

Referring again to FIG. 13, in an alternative method of implant insertion, the use of at least partially frusto-conical interbody spinal fusion implants allows for the creation of lordosis by the implant itself where none is present to begin with as with the angular relationship of $V_2$ and $V_3$ shown in FIG. 13. As per this example, the disc space $D_2$ which in the preferred circumstance would be fully distracted but need not be, but lacking lordosis, could have a bore drilled across that space such that equal arcs of bone $A_1$ and $A_2$ are removed from each of the adjacent vertebrae $V_2$ and $V_3$ using a drill 820 or bone milling device capable of producing a cylindrical bore. Where one such boring is performed, it would generally be in the center line and directed from anterior to posterior. This might be appropriate for use in the cervical spine. More commonly and as generally would be the rule in the lumbar spine, a pair of bores would be so created from anterior to posterior, one to each side of the midline. The essential feature here is that the vertebrae $V_2$ and $V_3$, whether distracted from each other or not, are essentially lacking the full restoration of lordosis. The use of the substantially cylindrical bone drill 820 provides for the removal of a generally uniform thickness of bone from each of the adjacent vertebrae from anterior to posterior. The insertion of a frusto-conical implant, having a larger diameter at its trailing edge than at its leading edge, then forces the anterior aspects of the adjacent vertebrae apart more so than the posterior aspects where the diameter is lesser. This utilizes the implant to produce the desired lordosis.

The method for the insertion of the spinal fusion implants of the present invention from the posterior aspect of the spine is described in detail in U.S. Pat. No. 6,080,155 and is incorporated herein by reference. Further, in the method of inserting the implants of the present invention from the posterior aspect of the spine, it is possible to place the adjacent vertebrae in lordosis prior to the bone removal step.

Figure 14:
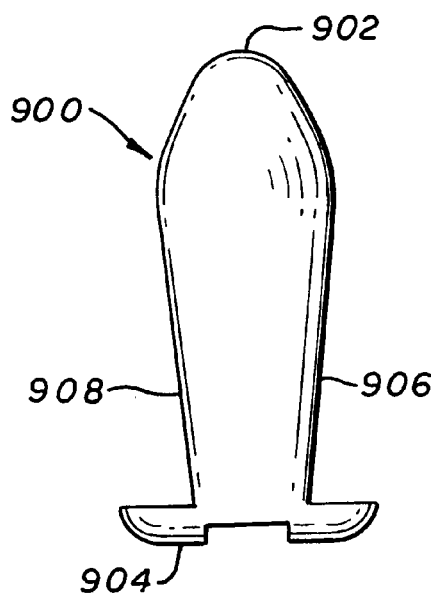
FIG. 14 is a side elevational view of the spinal distractor instrument of the present invention.
Figure 15:
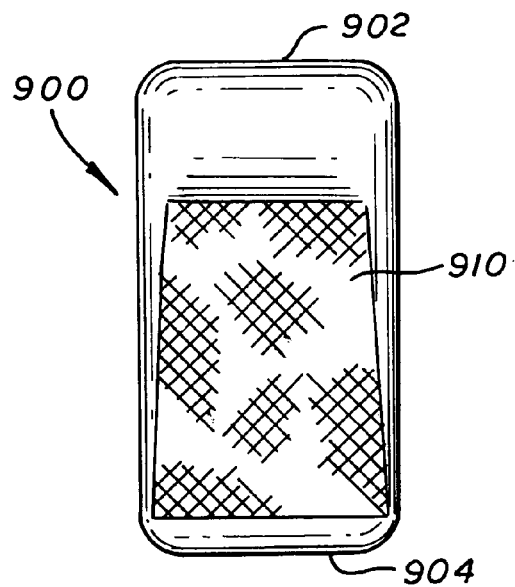
FIG. 15 is a top plan view of the spinal distractor instrument of FIG. 14.

Referring to FIGS. 14 and 15, spinal distractor 900 is shown which is used for distracting the adjacent vertebrae in lordosis prior to the bone removal step. The spinal distractor 900 has a tapered insertion end 902 to facilitate insertion, an instrument engaging end 904, and top and bottom surfaces 906 and 908. The top and bottom surfaces 906 and 908 are in a angular relationship to each other and are furthest apart at a point near the insertion end 902 to produce the desired lordosis when inserted in the disc space between two adjacent vertebrae. The top and bottom surfaces 906 and 908 have surface roughenings 910 for engaging the bone of the adjacent vertebrae and stabilizing the spinal distractor 900 when inserted.

While the present invention has been described in detail with regards to the preferred embodiments, it is appreciated that other variations of the present invention may be devised which do not depart from the inventive concept of the present invention. In particular, it is appreciated that the various teachings described in regards to the specific embodiments herein may be combined in a variety of ways such that the features are not limited to the specific embodiments described above.

Each of the features disclosed in the various embodiments and their functional equivalents may be combined in any combination sufficient to achieve the purposes of the present invention as described herein.

What is claimed is:

1. A method for inserting a spinal implant across a disc space between adjacent vertebral bodies of a human spine, said method comprising the steps of:
    distracting the adjacent vertebral bodies;
    forming a bore from the anterior or posterior aspect of the spinal column across the distracted disc space between the adjacent vertebral bodies and into the adjacent vertebral bodies, said bore having opposed arcuate portions in an angular relationship to one another along at least a portion of each of the adjacent vertebral bodies; and
    inserting into said bore said spinal implant having opposed arcuate portions in an angular relationship to one another along the length of said implant and oriented toward the adjacent vertebral bodies.

2. The method of claim 1, wherein said inserting step includes the sub-step of inserting said implant having a generally frusto-conical configuration.

3. The method of claim 2, wherein said inserting step includes the sub-step of inserting said implant having a generally round cross section transverse to the longitudinal axis of said implant.

4. The method of claim 1, wherein said inserting step includes the sub-step of inserting said implant having a generally oval cross section transverse to the longitudinal axis of said implant.

5. The method of claim 1, wherein said inserting step includes the sub-step of inserting said implant having at least one truncated side.

6. The method of claim 1, wherein the distracting step includes the sub-step of inducing angulation to the adjacent vertebral bodies.

7. The method of claim 1, wherein the distracting step includes the step of inserting a spinal distractor into the disc space between the adjacent vertebral bodies.

8. The method of claim 7, further comprising the step of positioning a sleeve over said spinal distractor and into contact with the adjacent vertebral bodies.

9. The method of claim 1, wherein the distracting step includes the step of positioning a sleeve having an extension so that the extension is inserted into the disc space and bears against end plates of the adjacent vertebral bodies.

10. The method of claim 9, wherein the step of inserting includes the sub-step of inserting said implant through said sleeve and into the bore.

11. The method of claim 9, wherein the positioning step includes the sub-step of inducing angulation to the adjacent vertebral bodies.

12. The method of claim 1, wherein the forming step includes the sub-step selected from one of milling and drilling the bore.

13. The method of claim 1, wherein the forming step further comprises the sub-step of placing a drill having a diameter greater than the disc space through said sleeve prior to the sub-step of drilling.

14. The method of claim 1, further comprising the step of loading said implant with a material selected from one of a fusion promoting substance, a bone growth promoting material, bone morphogenetic protein, and bone prior to the step of inserting.

15. The method of claim 1, further comprising the step of coating said implant with a material selected from one of bone morphogenic protein, a fusion promoting substance, and a bone growth promoting material prior to the step of inserting.

16. The method of claim 1, wherein the step of inserting includes inserting an implant containing a material selected from one of a fusion promoting substance, a bone growth promoting material, bone morphogenetic protein, and bone.

17. The method of claim 1, wherein the step of inserting includes inserting an implant comprising a material selected from one of a bone growth promoting material, bone morphogenetic protein, and bone.

18. The method of claim 1, wherein the step of inserting includes inserting an implant in combination with a material selected from one of a bone growth promoting material, bone morphogenetic protein, and bone.

19. The method of claim 8, further comprising the step of placing an inner sleeve within said sleeve prior to the step of forming the bore.

20. The method of claim 19, further comprising the step of removing said inner sleeve prior to the step of inserting said implant.

21. A method for preparing a spinal disc space between a pair of vertebral endplates for insertion of an implant therebetween, comprising:
    inserting a guide sleeve to the disc space from an anterior approach, the guide sleeve having a working channel providing access to a first disc space location and a second disc space location;
    distracting the disc space to a desired disc space height;
    preparing the first disc space location through the working channel for insertion of a first implant therein;
    inserting a reamer plug through the working channel into the first disc space location;
    preparing the second disc space location through the working channel for insertion of a second implant therein after inserting the reamer plug;
    inserting the second implant through the working channel into the second disc space location, the second implant being tapered to establish a desired lordotic angle between the vertebral endplates;
    removing the plug from the first disc space location after inserting the second implant; and
    inserting the first implant through the working channel into the first disc space location, the first implant being tapered to establish a desired lordotic angle between the vertebral endplates.

* * * * *

UNITED STATES PATENT AND TRADEMARK OFFICE
CERTIFICATE OF CORRECTION

PATENT NO. : 7,291,149 B1  Page 1 of 1
APPLICATION NO. : 09/412082
DATED : November 6, 2007
INVENTOR(S) : Gary Karlin Michelson It is certified that error appears in the above-identified patent and that said Letters Patent is hereby corrected as shown below:

<u>Title Page, ITEM (56) References Cited</u>:
U.S. Patent Documents, after line 21: add -- 5,279,292 01/1994 Baumann --;
Foreign Patent Documents, first column, line 13: change "9/1985" to -- 4/1986 --;
Foreign Patent Documents, second column, line 13: delete "FR 0 179 695 4/1986";
Foreign Patent Documents, second column, after line 15: Insert the following:
            -- GB 1291470 10/1972
              GB 1492990 11/1977
              GB 1531487 11/1978 --; and
Other Publications, line 7, change "Compressiion" to -- Compression --.

<u>Title Page, ITEM (56) References Cited</u>:
Other Publications, second column, line 2, change "Phychiatry" to -- Psychiatry --.

<u>Column 18</u>:
Line 10: change "morphogenic" to -- morphogenetic --.

Signed and Sealed this

Fourth Day of March, 2008

JON W. DUDAS
*Director of the United States Patent and Trademark Office*